United States Patent
Kiselyov et al.

(10) Patent No.: US 12,059,242 B2
(45) Date of Patent: Aug. 13, 2024

(54) HYBRID ELECTROMAGNETIC DEVICE FOR REMOTE CONTROL OF MICRO-NANO SCALE ROBOTS, MEDICAL TOOLS AND IMPLANTABLE DEVICES

(71) Applicant: BIONAUT LABS LTD., Herzliya (IL)

(72) Inventors: Alex Kiselyov, San Diego, CA (US); Michael Shpigelmacher, Los Angeles, CA (US); Eran Oren, Tel-Aviv (IL); Alexander Sromin, Ashdod (IL); Nadav Cohen, Haifa (IL); Amitay Peleg, Haifa (IL); Eli Van Cleve, Los Angeles, CA (US)

(73) Assignee: BIONAUT LABS LTD. (IL)

(*) Notice: Subject to any disclaimer, the term of this patent is extended or adjusted under 35 U.S.C. 154(b) by 690 days.

(21) Appl. No.: 17/052,241

(22) PCT Filed: May 2, 2019

(86) PCT No.: PCT/US2019/030345
§ 371 (c)(1),
(2) Date: Nov. 2, 2020

(87) PCT Pub. No.: WO2019/213362
PCT Pub. Date: Nov. 7, 2019

(65) Prior Publication Data
US 2021/0052190 A1 Feb. 25, 2021

Related U.S. Application Data

(60) Provisional application No. 62/666,536, filed on May 3, 2018.

(51) Int. Cl.
*A61B 5/05* (2021.01)
*A61B 5/055* (2006.01)
(Continued)

(52) U.S. Cl.
CPC .............. *A61B 5/062* (2013.01); *A61B 5/055* (2013.01); *A61B 34/30* (2016.02); *A61G 13/10* (2013.01);
(Continued)

(58) Field of Classification Search
CPC .............. A61B 5/062; A61B 5/055; A61M 2205/3317; A61M 2205/6054; G01R 33/287; G01R 33/54; G01R 33/383
See application file for complete search history.

(56) References Cited

U.S. PATENT DOCUMENTS 3,358,676 A 12/1967 Frei et al.
6,348,070 B1* 2/2002 Teissl ................. A61N 1/36038
623/24
(Continued)

FOREIGN PATENT DOCUMENTS

JP 2005103091 4/2005
JP 2006062071 3/2006
JP 2007-215583 8/2007

OTHER PUBLICATIONS

Zheng et al., "An overview of magnetic micro-robot systems for biomedical applications", Microsystem Technologies 2016, vol. 22, No. 10 pp. 2371-2387.
(Continued)

*Primary Examiner* — Joel F Brutus
(74) *Attorney, Agent, or Firm* — Mark S. Cohen; PEARL COHEN ZEDEK LATZER BARATZ LLP

(57) ABSTRACT

Apparatus and systems for providing magnetic fields for controlling micro-devices implanted in a patient body, organ, or tissue. Novel coil configurations are disclosed which provide magnetic fields of adequate strength and directional characteristics over a large operational region with minimal weight and power dissipation, while providing ease of access to the focus regions. Also provided are
(Continued)

micro-devices in various size regimes which can be controlled both in position as well as in function (such as release of therapeutic materials), and which are capable of both energy and data transfer with the magnetic field control system.

15 Claims, 40 Drawing Sheets

(51) Int. Cl.
| | |
|---|---|
| A61B 5/06 | (2006.01) |
| A61B 34/30 | (2016.01) |
| A61G 13/10 | (2006.01) |
| A61M 5/142 | (2006.01) |
| G01R 33/28 | (2006.01) |
| G01R 33/383 | (2006.01) |
| G01R 33/54 | (2006.01) |

(52) U.S. Cl.
CPC ....... *A61M 5/14276* (2013.01); *G01R 33/287* (2013.01); *G01R 33/383* (2013.01); *G01R 33/54* (2013.01); *A61M 2205/3317* (2013.01); *A61M 2205/6054* (2013.01)

(56) References Cited

U.S. PATENT DOCUMENTS

| | | | |
|---|---|---|---|
| 2005/0093544 A1 | 5/2005 | Ries | |
| 2005/0245811 A1* | 11/2005 | Scheffler | G01R 33/287 600/410 |
| 2008/0049372 A1 | 2/2008 | Loke | |
| 2009/0206837 A1* | 8/2009 | Teklemariam | G01R 33/383 324/309 |
| 2010/0298635 A1* | 11/2010 | Hata | A61B 1/00158 600/104 |
| 2012/0281330 A1 | 11/2012 | Abbott et al. | |
| 2012/0310034 A1 | 12/2012 | Creighton et al. | |
| 2013/0060130 A1 | 3/2013 | Park et al. | |
| 2013/0072789 A1 | 3/2013 | Park et al. | |
| 2014/0225694 A1 | 8/2014 | Sitti et al. | |
| 2015/0229194 A1 | 8/2015 | Sromin | |
| 2016/0111192 A1 | 4/2016 | Suzara | |
| 2016/0223626 A1 | 8/2016 | Schmale | |
| 2016/0262841 A1* | 9/2016 | Park | A61B 34/73 |
| 2016/0298630 A1 | 10/2016 | Sitti et al. | |
| 2017/0000946 A1* | 1/2017 | Boyle | A61B 17/42 |
| 2017/0133900 A1* | 5/2017 | Guina | H02K 21/02 |

OTHER PUBLICATIONS

Supplementary European Search Report dated Dec. 23, 2021 in respect of EP Application No. 19795961.2.
Extended European Search Report dated Sep. 30, 2022 in respect of EP Application No. 22179063.7.
Notice of Allowance dated Nov. 22, 2022 in respect of Japanese Patent Application No. 2021-510276 with English translation.
International Search Report dated Jul. 3, 2019 in respect of PCT Int'l Application No. PCT/US2019/030345.

* cited by examiner 48-rod single-layer magnetic system

Grouping in single-layer magnetic systems

Generating maximal vertically directed field

Generating decreased vertically directed field

Entire system 48-rods and solenoid

HYBRID ELECTROMAGNETIC DEVICE FOR REMOTE CONTROL OF MICRO-NANO SCALE ROBOTS, MEDICAL TOOLS AND IMPLANTABLE DEVICES

FIELD

The invention is in the field of electromagnetic control devices.

BACKGROUND

Remote control of a medical device inside the human body (herein denoted as an "internal device") can be useful for a variety of purposes, including delivery of therapeutic payloads, diagnostics or surgical procedures. Internal devices include without limitation micro- or nano-scale robots, medical tools, implantable devices, "smart pills", micropumps, etc. Electromagnetic mechanisms for remote control of internal devices are known in the literature and in practice, where an electro-magnetic device external to the body (herein denoted as an "external device") is used to control the internal device's motion, communicate with the internal device (uplink and downlink communication), transfer energy to the internal device, track the internal device, and provide other types of functionality.

SUMMARY

An objective of embodiments of the present invention is to address the challenges associated with designing such systems which are lightweight, with few or no moving parts, consume little power, generate diverse electro-magnetic field configurations, provide therapeutic and/or diagnostic functionality, work in an integrated fashion with other therapeutic modalities including therapeutics delivery and imaging modules and adhere to medical safety regulations in terms of power supply, noise and temperature. Embodiments according to the invention provide an external control system, allowing the following types of functionality:

Remote control of internal device motion via generation of rotating magnetic field, permanent magnetic field or a combination of thereof with specific field parameters that could be expeditiously customized and amended as described below.

Remote control including navigation including propulsion via sophisticated 3D trajectories, time resolved (e.g., rapid, gradual) stop-and-go motion, forward and backward motion of internal device via generation of magnetic field gradients, with specific field parameters that are customized to attain the following:

remote control of internal device motion via generation of arbitrary magnetic fields, for mechanical actuation of internal device components as disclosed herein;

integration with respective modules to control internal device components and effect imaging;

remote and controlled energy transfer, energy storage and/or conversion and propulsion of an internal device;

remote and controlled release of a targeted therapeutic agent from an internal device;

remote complex navigation to a target destination within the target, and subsequent retraction of an internal device to a general collection point;

data communication with an internal device (uplink/downlink);

simultaneous or decoupled electromagnetic tracking to locate an internal device;

compatibility with auxiliary devices used in relevant medical procedures, such as medical imaging devices, anesthesia tubing, access for surgical equipment, etc.;

ease of procedure for patient and physician, including facile access to a patient and operational safety; and data monitoring, logging and control via a remote control station.

One embodiment of the invention provides an electromagnetic control system for remote control of a micro-scale device, the control system including: a first subsystem generating a magnetic field in an operational region, comprising two or more magnetic field generating devices proximate but not entirely enclosing the operational region; the magnetic field generating devices generating overlapping flux lines generating a combined field vector in three dimensions; and an imaging system adapted to track a location of the micro-scale device; and an interface adapted to receive input from the imaging system and to transfer energy to the coils to direct movement of the micro-scale device in the magnetic field.

In one embodiment, this invention provides an electromagnetic control system for remote control of a micro-scale device, the control system comprising: a first subsystem generating a magnetic field in an operational region, comprising two or more magnetic field generating devices proximate but not entirely enclosing the operational region; the magnetic field generating devices generating overlapping flux lines generating a combined field vector in three dimensions; and an imaging system adapted to track a location of the micro-scale device; and an interface adapted to receive input from the imaging system and to transfer energy to the coils to direct movement of the micro-scale device in the magnetic field.

In one embodiment, this invention provides an electromagnetic control system for remote control of a micro-scale device, the control system comprising: a first subsystem generating a magnetic field in an x-y plane of an operational region having x y and z axes, comprising a Halbach array of permanent magnets oriented around the z axis; a solenoidal coil around the z axis; and an imaging system adapted to track a location of the micro-scale device; and an interface adapted to receive input from the imaging system and to transfer energy to the coils to direct movement of the micro-scale device in the magnetic field.

In one embodiment, this invention provides an electromagnetic control system for remote control of a micro-scale device, the control system comprising: a first subsystem generating a magnetic field in an operational region, comprising a U-shaped coil; an imaging system adapted to track a location of the micro-scale device; and an interface adapted to receive input from the imaging system and to transfer energy to the coils to direct movement of the micro-scale device in the magnetic field.

In one embodiment, this invention provides a system comprising an electromagnetic system described herein; and at least one micro-scale device having a dimension of 1 nm to 10 mm and having a magnetic moment and adapted to be implanted in a body.

In one embodiment, this invention provides a method of directing movement of a device in a patient body, comprising: providing an electromagnetic system described herein, and at least one micro-scale device having a dimension of 1 nm to 10 mm and having a magnetic moment and adapted to be implanted in a body; and applying a magnetic field generated by the electromagnetic control system to the micro-scale device to direct movement of the micro-scale device in the magnetic field.

The term "patient body" herein denotes an entity under examination, analysis, diagnosis, and/or therapeutic treatment, and includes without limitation: animal bodies, organs, tissue, and specimens thereof, including the human body, organs, tissue, and specimens thereof, whether living or not.

This application contains several embodiments of systems with these functionalities, some of which include hybrid external devices, relying on electromagnetic mechanisms as well as acoustic or optical mechanisms.

BRIEF DESCRIPTION OF THE DRAWINGS

The subject matter regarded as the invention is particularly pointed out and distinctly claimed in the concluding portion of this specification. The invention, however, both as to organization and method of operation, together with objects, features, and advantages thereof, may best be understood by reference to the following detailed descriptions when read with the accompanying drawings in which:

DETAILED DESCRIPTION OF THE INVENTION

Figure 1A:
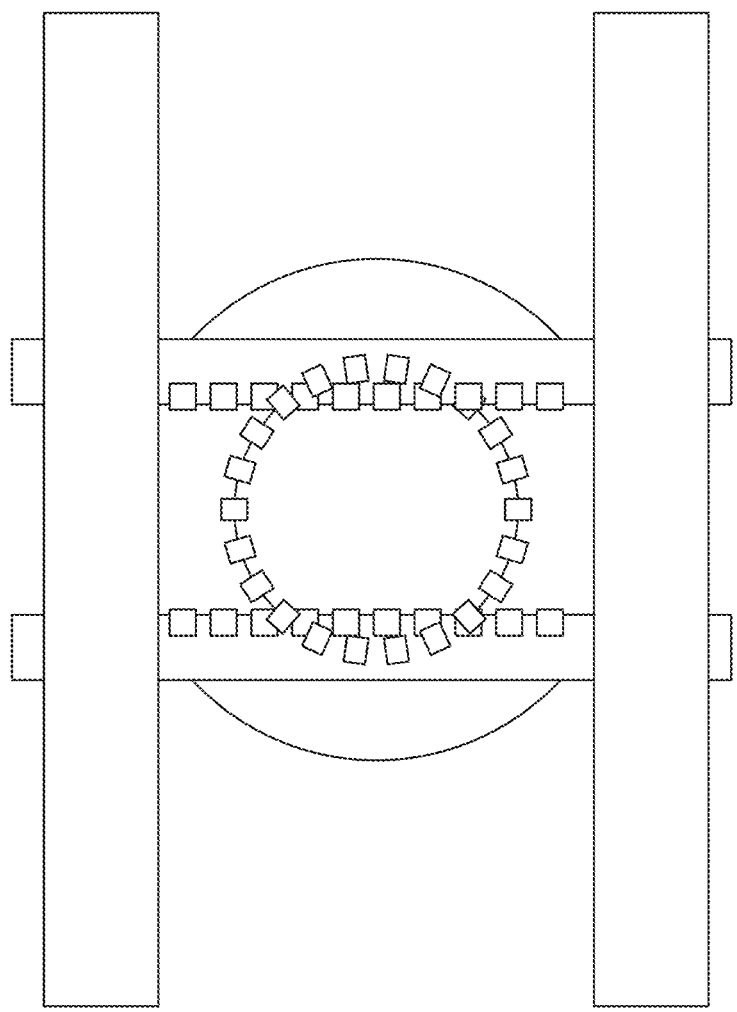
FIG. 1-FIG. 25 illustrate embodiments of the invention described in the present application.

In the following detailed description, numerous specific details are set forth in order to provide a thorough understanding of the invention. However, it will be understood by those of ordinary skill in the art that the present invention may be practiced without these specific details. In other instances, well-known methods, procedures, and/or components have not been described in detail so as not to obscure the present invention.

In one embodiment the invention is a coil-based system, providing a magnetic field in a large work space, to be used for motion control.

In this embodiment, the coils are designed in a manner allowing for generation of a magnetic field in the range of 50 Gauss-1,500 Gauss, and representative continuous absolute fields of up to 500 Gauss in a cylindrical, conical or alternative operational region (treatment volume) of up to 50 cm in length and up to 120 cm in diameter, where the generated field can be rotating, fixed, pulsed, time varying with an arbitrary analytical form, or a gradient in 3D space and typical rotational frequencies in the interval of 0.5 Hz-60 Hz.

The operational region of the system is based on patient body size, such as for a human or a large animal.

In an embodiment of the invention, a control system changes magnetic field amplitude to drive the motion of (micro)mechanical components of the internal device, generating forward, backward, stop-and-go, and complex 3D motion in homogeneous and heterogeneous matrices.

The aforementioned design produces electro-magnetic field lines allowing for a reliable, reproducible, hi-fidelity propulsion of an internal device.

The aforementioned design may yield a magnetic field gradient. For example, by using an element with a magnetic moment of 10-4 Nm/T, the design allows applying a magnetic field with typical gradients in the order of 50 mT/m over volumes exceeding or equal to 1 $cm^3$ to afford typical forces exceeding micro-Newtons. Typical configurations include, but are not limited to, Maxwell coils to secure high volume of linear gradient for a simpler field rectification and control. In various embodiments, a Maxwell coil or combination thereof is part of a setup that includes three pairs of Helmholtz coils and/or a combination of Helmholtz coils and fixed magnets.

The aforementioned magnetic field gradient could to be a one-to-one function of three-dimensional space to accommodate sensing of device location by an internal device, utilizing a built-in magnetic gradient sensor that accurately detects gradients at 1 mT/m or better as exemplified by but not limited to diverse micromechanical devices including MEMS cantilever devices as exemplified in Dabsch, A., et al. "MEMS cantilever based magnetic field gradient sensor". The resulting position can be communicated back to the external device using methods described below, serving as a tracking mechanism for location of internal device. In addition, the described magnetic field gradient may be applied to a controlled release of therapeutic load mediated by electromagnetic field-sensitive materials.

Figure 1B:
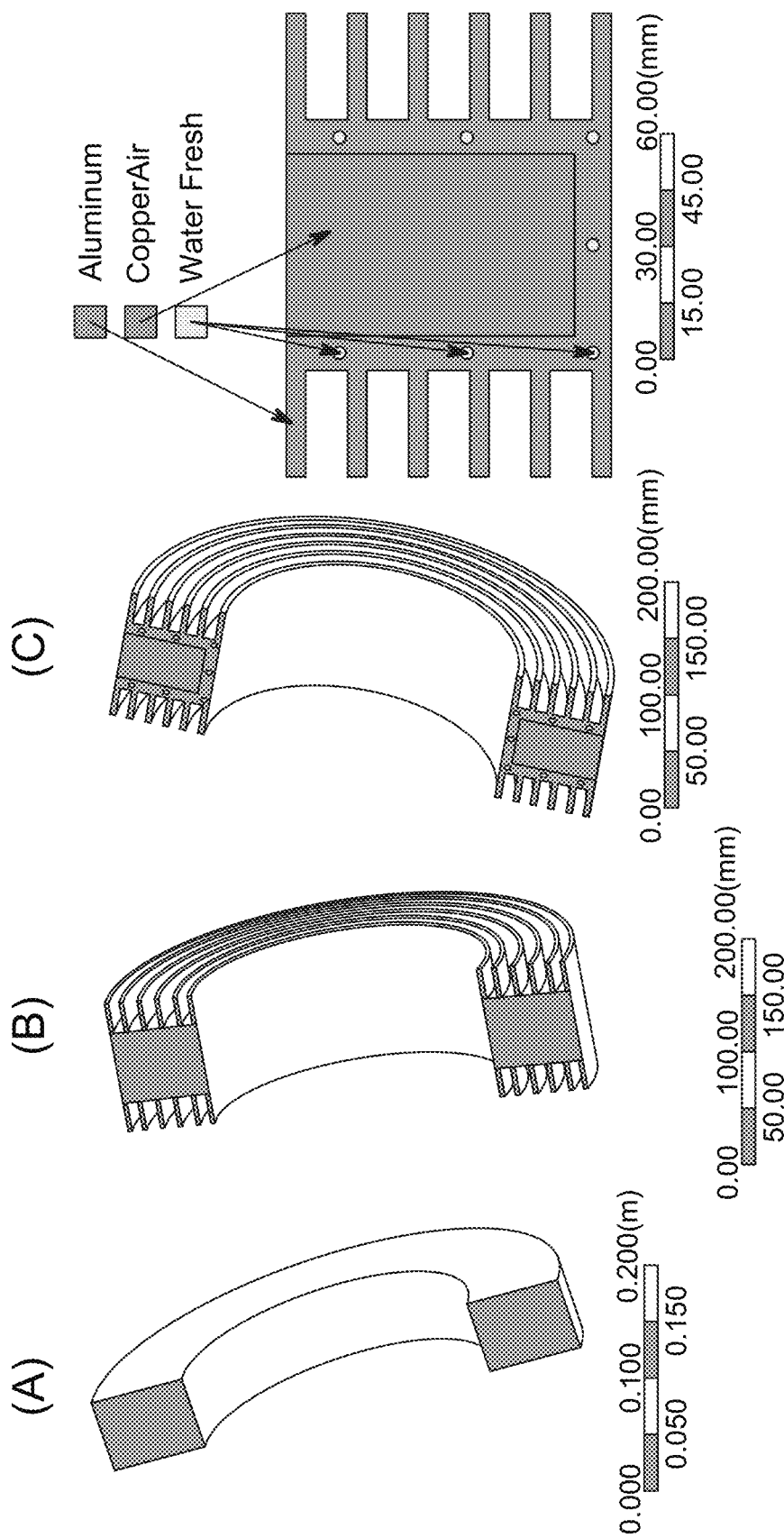

In an embodiment of the invention, a Helmholtz configuration is applied. Specifically, at least one pair of coils, and typically three pairs of coils generate a magnetic field as per voltage and current supply (FIG. 1 A). The aforementioned coils are ordered in a manner where each coil pair acts as poles to create a rotating magnetic field. Two coil pairs create rotating magnetic field in their plane and thus induce a rotational motion that translates into a linear force and motion in the perpendicular vector. A 3 coil-pair system can generally point to any direction in a 3D space and generation of rotating field in any direction is straightforward. In related embodiments, the aforementioned coil topology includes circular, square, and alternative geometries to accommodate operational opening and engineering convenience.

In an embodiment of the invention, the coil system is made of a high-conductivity metal, non-limiting examples of which include copper, aluminum and/or their alloys, thereby exhibiting a high ratio of conductivity to weight. Related embodiments utilize carbon nanotube (CNT) wires, silver, and gold. Coils are typically made of multiple wires held together using resins exemplified by epoxy adhesive, silicone, and the like. The aforementioned wires are insulated or laminated to prevent short circuits. A typical system weighs between 100 Kg and 500 Kg, where most of the weight is in the metal coil and coil contour/topology components.

In various embodiments, a mechanical structure secures the coils in a specific 3D topological configuration, to withstand gravity and forces exerted between them due to the magnetic field. The structural components are of a non-ferromagnetic metal such as aluminum, but in related embodiments are in part or in whole high density plastics, ceramics, carbon fiber composite materials, and the like.

In certain embodiments, the system is cooled in order to prevent overheating, and to allow for higher current densities in the wires to increase the targeted operational magnetic fields. Cooling is performed by thermally conductive liquids including but not limited to distilled water, glycols, dielectric fluids (Fluorinert, PAO) by letting it flow in, around or in between the coils' wires to remove the dissipated heat. In related embodiments, cooling is performed by generating air or other gas flow in, around, or between the wires. In particular embodiments, cooling ducts are the free volume around the wires, and have a ribbed geometry for better thermal conductance and dispersion via convection (FIG. 1 B). In some embodiments, the wires, ducts or other materials such as aforementioned epoxy resins thermally communicate with heatsink materials through thermal grease or similar thermal coupling material. The resulting temperature on the external surfaces of the ducts is typically 40° C. or less to meet safety requirements and regulations.

Typical sizes of the system include the smallest set of coils with diameters of 40 cm-60 cm, to accommodate introducing a patient or a patient lying in a bed through the created orifice. Larger coil pairs have typical diameters of 80 cm-120 cm, where dimensions refer to coil size, including surrounding cooling ducts. The specified sizes with the resulting weight allows for easy transportation and installation in hospital rooms or clinical spaces.

In various embodiments, coil planes are perpendicular or parallel to the ground or gravity vector, and in related embodiments the system is set at an angle to direction of gravity, thus providing a more accommodating orifice for the long dimension of a patient body cross section.

Electrical power supply to the aforementioned coils configuration is typically provided by an inverter, a converter, or a rectifier to supply varying levels of AC or DC current with characteristic values of 50 V-100 V, consuming characteristic power of 5 kW-7 kW per coil at peak consumption, while generating magnetic fields of approximately 500 Gauss in the central volume between the coils. The power supply may or may not include additional capacitors to allow for the electrical requirements. In a preferred embodiment, a power capacitor bank is included connected in series to some or all of the coils to use resonance to pass a desired frequency. The capacitor bank is varied to change its effective capacitance. Characteristic input electrical frequencies are between 0 Hz and 50 Hz and are synchronous with internal device motion. However, in some cases a higher frequency can be used such as using 100 Hz to induce additional mechanical motion and/or to move with a high slip (discrepancy between electrical and mechanical rotational velocities). The electrical supply is controlled by a computer system that uses prior data to calculate the required currents for a desired magnetic field, rotational speed, or gradient.

In embodiments of the invention, the device is used in conjunction with a single or multiple magnetic field sensors for calibration, real-time correction and verification of the magnetic output. The sensors can be set separately or connected to aforementioned computer system to provide control over the electrical components.

Figure 2A:
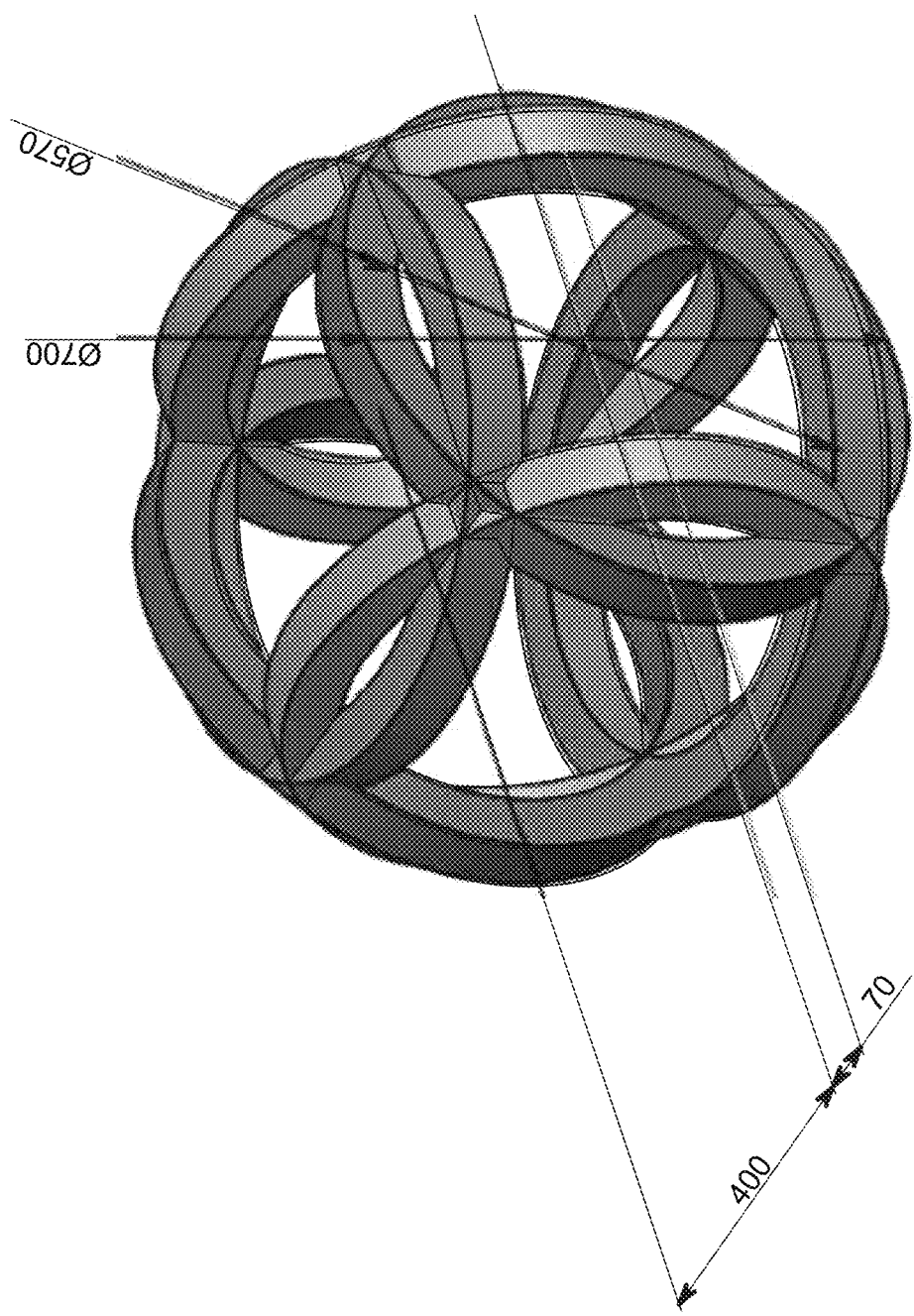
Figure 2B:
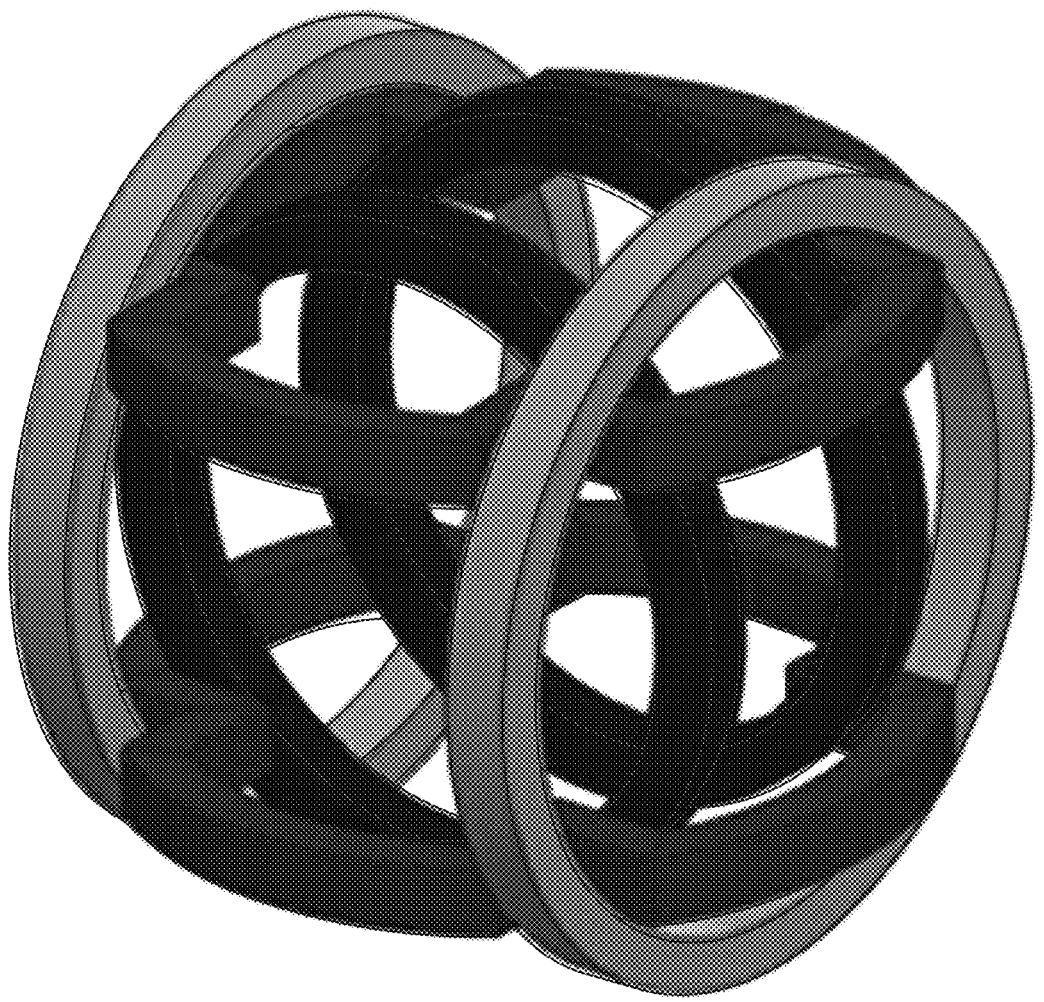
Figure 3:
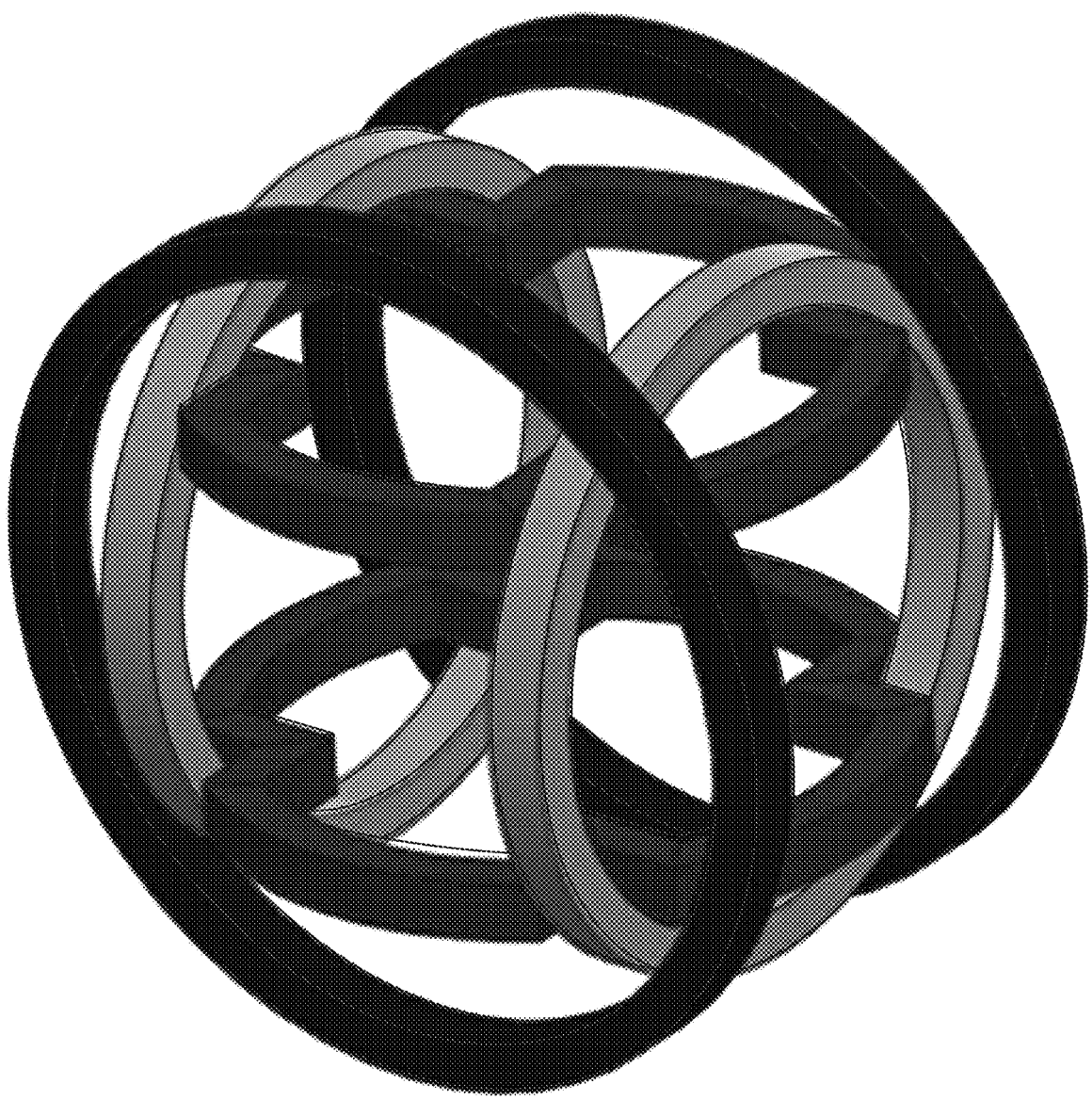

To limit weight, provide better calibrated magnetic field in the operational volume or to accommodate specific design considerations, additional embodiments utilize alternative coil configurations. In a non-limiting example, structural indentation is added to the 3D set-up to allow a smaller form factor of external coils. The aforementioned indentation shows a curvature radius proportional to the coils width when taking an external duct into account (FIG. 2B, FIG. 3). The indentations are limited to maintain uniformity of the magnetic field in the central volume to an acceptable level, such as a uniformity of up to 5% of the central magnetic field strength over a volume of 20 cm×20 cm×20 cm, sufficient for robust motion control inside a patient body.

In an alternative embodiment, the coils are intertwined to create larger intersections between the coils. In this case, all 6 coils in a 3 coil-pairs configuration have the same diameter (see FIG. 2A, FIG. 2B). In another alternative embodiment, only 4 of the 6 coils have the same diameter (see FIG. 3). In this case, cooling ducts can be shared between the coils (a single connected volume).

An embodiment of the invention provides for assembly of the device from a set of multiple modular parts connected with fasteners (such as bolts) that allows simple assembly and disassembly. In a related embodiment, the coils are not moved after assembly. In other embodiments, the coils' orientation with reference with the patient and/or the patient's bed is modulated by moving it on a gimballed bearing that allows 1 or 2 degrees of freedom in azimuth, tilt, or both. Alternatively, the patient's bed can be gimballed in a similar manner to allow changes in the orientation of the patient with respect to the coil system.

In some configurations, some of the coils are connected to hinges that allow moving them in such a manner that enables a patient to be easily inserted to the central operational volume between them.

Other embodiments include a bed that is inserted into the central operational region with or without the patient body, by pushing it inside and having the wheels or other parts of it fold or fit into tracks to prevent the need for otherwise moving the patient body. In further embodiments, the bed and the electromagnetic device are arbitrarily movable in relation to each other in 3D, using mechanical manipulators or motors controlled by a central control system, which may be connected to an external imaging system as well as to the electromagnetic device. In certain embodiments, the electromagnetic device controls the motion of an internal device inside patient body, in a specific unit volume ("focus region") in patient body where field generated by electromagnetic device is sufficiently strong. As the internal device moves, it may move outside of the focus region. Hence, there is a need to image the internal device using an imaging system (e.g., ultrasound, X-Ray, or other imaging modalities), and then adjust the location of the electromagnetic device in relation to patient body so the focus region follows the location of the internal device as it moves. Throughout this process, the signal generated by the electromagnetic device is continuously controlled, to ensure proper movement of internal device via tissue.

Certain embodiments provide, in addition to the Helmholtz coils described herein, other coils such as Maxwell coils in order to create a more uniform magnetic field or a field gradient. In related embodiments multiple coil pairs are used in such a way that several of them are active at any given moment to create the desired spatial distribution of magnetic field. The coils are positioned around the patient's bed and are modular to accommodate specific operational needs, including but not limited to delivery of therapeutic particles following a specific trajectory in a specific biological matrix, tissue, or organ. Related embodiments use a ferromagnetic core to lead and focus the generated magnetic field to points closer to the patient body.

Certain embodiments utilize cryogenic superconducting materials to provide higher flux densities and stronger magnetic fields. Such superconductors typically work with peak magnetic fields in the order of 1 Tesla, and liquid nitrogen or liquid helium cooling.

The aforementioned embodiments also include high-frequency fields in the order of KHz or above to induce particle heating and hyperthermia-like effects to induce enhanced propulsion by changing the local viscosity properties of the matrix, tissue, or organ in an asymmetric manner, or by changing the material properties to enable motion with less resistance.

Figure 4:
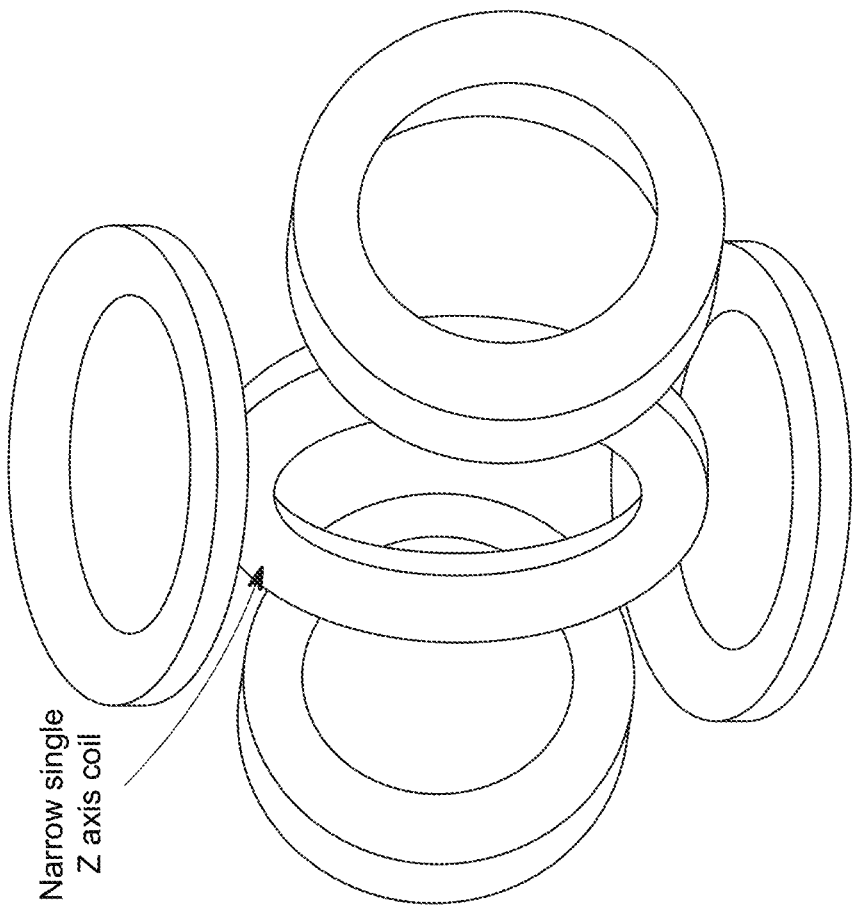

In a specific embodiment, only a single, narrow coil is used to generate the field component parallel to the human body symmetry axis (defined as the z-axis) (FIG. 4). This is reasonable, as the strength of the field is maximal at the central region (defined as the focus region). If a movable internal device is present in the focus point, as it shifts along z-axis, it may be necessary to shift the focus point along z-axis to follow the internal device motion. In a related embodiment this is implemented by shifting the patient or the electromagnetic device along this axis in relation to one another. Utilizing a single narrow coil in the z-axis instead of two larger coils allows minimizing the weight, cooling and power requirements of the system.

Figure 5:
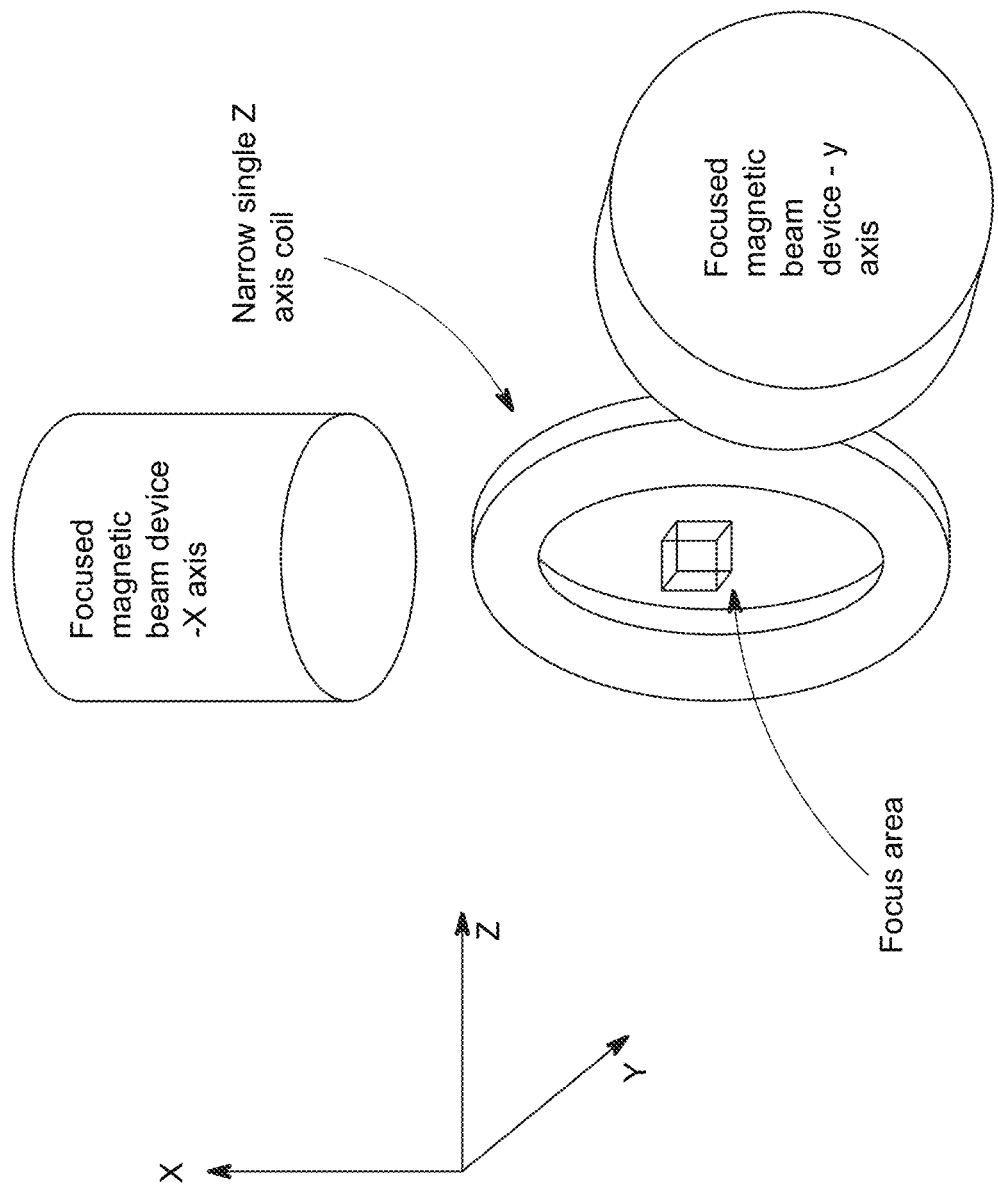

In specific embodiments, focused magnetic beams are used in the x-, y-, or z-axis instead of or in addition to standard Helmholtz/Maxwell coils, or in addition to a single narrow coil in the z-axis, for minimizing the weight of the system while generating a strong magnetic field only in a small focus region inside a patient body (FIG. 5).

In specific embodiments, other magnetic field-focusing structures are placed between the electromagnetic device and the patient body, to focus magnetic field lines toward the target focus region where an internal device is placed inside patient body. Field-focusing structures include, but are not limited to ferrite conical or trapezoidal structures with the narrow tip pointing towards the patient body, as well as other materials and topologies.

Another embodiment provides a coil-based system, allowing remote power transfer to the internal device using electromagnetic means. A related embodiment provides a coil system for remote power transfer to an internal device such as a nano or microrobot or an implant, in addition to induced motion capabilities as described herein. These embodiments work in conjunction with an internal element such as an inductive coupled coils system, a resonant inductive system, a magneto-dynamic rotational coupling system, and the like. The internal element receives the energy transmitted by the external coil system via the generated magnetic field, changes in the magnetic field (quasi-static, non-radiative), or through radio-frequency emitted radiation.

The coils apply varying magnetic field of MHz to GHz frequencies to transmit energy that is captured by the internal device. In other embodiments, a rotational magnetic field with frequencies up to 100 Hz are applied to induce mechanical motion that is converted into electrical energy, propulsion, or energy storage.

Additional embodiments provide for modulating the aforementioned low, intermediate and high frequencies as well as the magnetic field described. This is commonly used in conjunction with additional power electronics components that provide impedance matching (such as capacitors, coils or transistor switches). In related embodiments, energy transfer is continuous, in bursts or semi-continuous over periods of time when using the coils during an operation. In some embodiments, the configuration is identical to that previously-described, or based on additional sets of coils and/or permanent magnets. In a related embodiment, energy transfer is achieved via heating a component such as magnetic nanoparticles (MNPs) by inducing hyperthermia-like effect and utilizing the electro-thermal effect to induce voltages.

Another embodiment provides a coil-based system having uplink/downlink communications with the internal device using electromagnetic means. This coil-based system provides data transfer in addition to magnetically-induced propulsion and/or magnetic energy transfer, or may be used separately for communications with the internal device. In order to accommodate this functionality, the internal device is equipped with a receiving component and/or a transmitting component for information transfer. In a non-limiting example, the internal device has a radio-frequency identification (RFID) integrated circuit that collects data during motion inside a patient body, report device position, and/or provide feedback on device status. As commanded by external signals, the device can release therapeutic substances, carry out mechanical motion, heating or self-destruct. Digital and/or analog RF based protocols can be used.

According to various embodiments, transmitting information is accomplished via the same coil configuration as described previously herein or with additional coils or fixed magnets. It can be also used in a stand-alone manner decoupled from the propulsion described above, or by modulating the additional information transmitted on the same magnetic field signal. Information transfer is used directly with the nano-/microrobot, as well as with smart pills, implants, micro-implants, catheters and other imaging or therapeutic devices. All devices operate separately and/or work in parallel to the nano-/microrobot.

A goal of the magnetic systems described herein is to generate a magnetic field at any point in the patient body (defined as the operational region), while allowing easy access to patient body during procedure for monitoring of patient vital signs and tracking devices inside the body, using applicable imaging devices (such as ultrasound, X-Ray, etc.). At the same time, the system offers a practical cooling solution and adheres to weight and power consumption limitations. Assuming the size of a large male patient, the operational region may be 50 cm×50 cm×50 cm or more.

Systems according to embodiments of the present invention meet weight-power-access-size-cooling requirements, whereas conventional coil-based system (e.g., using 3 pairs of orthogonal Helmholtz coils enclosing the patient body) become hot and dissipate excessive heat, requiring extensive cooling. In addition, conventional systems are very heavy (weighing a ton or more). For reference, commercially available MRI systems often require liquid nitrogen cooling and also weigh as much as a ton or more, significantly limiting the ability to install them in standard building locations anywhere above a ground floor or requiring reinforced construction. Systems according to embodiments of the present invention have reduced weight in the single 100s of kilograms or less, making them ideal for practical solutions.

EXAMPLES

Augmented Levitation Table

Figure 6A:
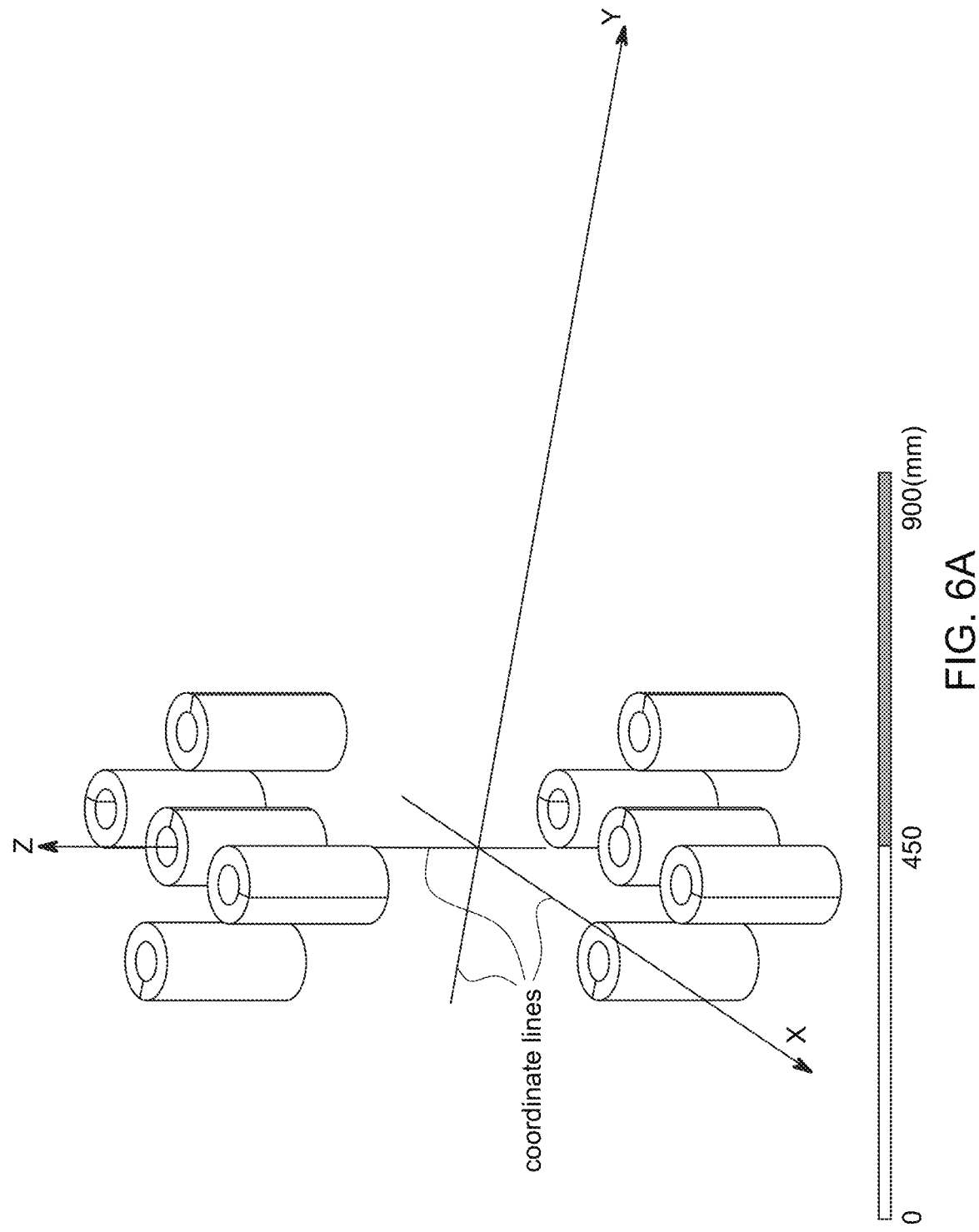
Figure 6B:
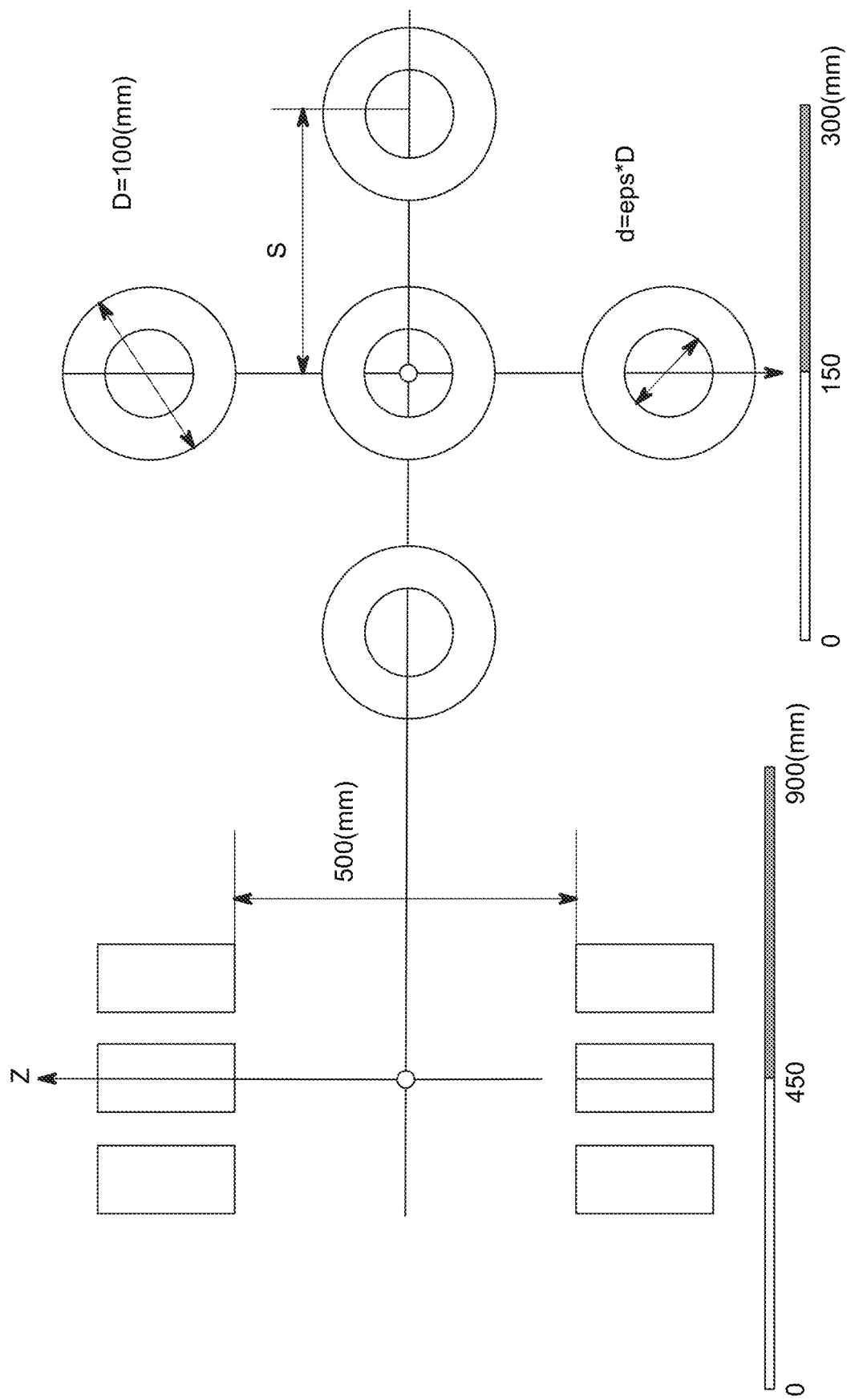
Figure 6C:
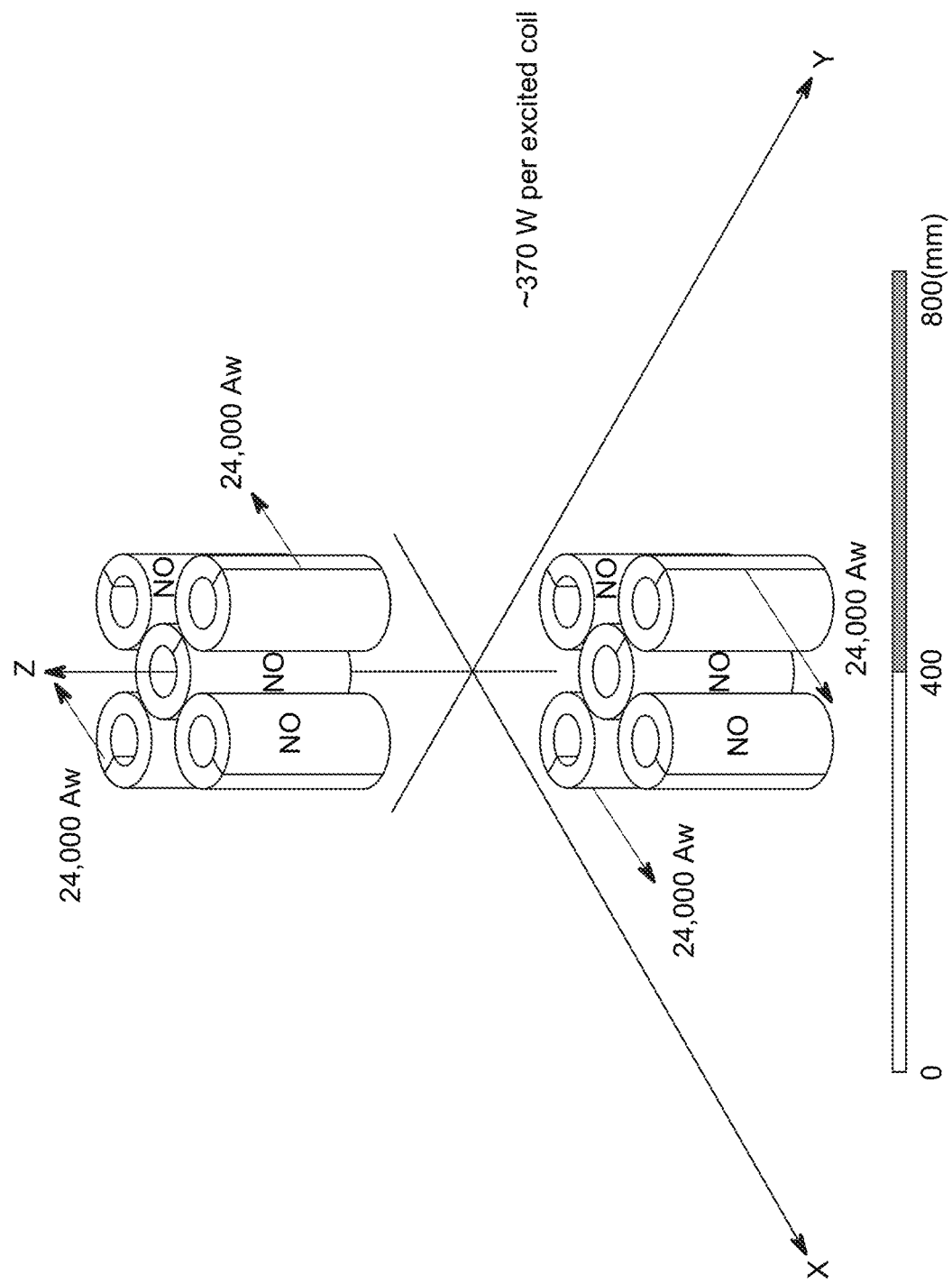
Figure 6D:
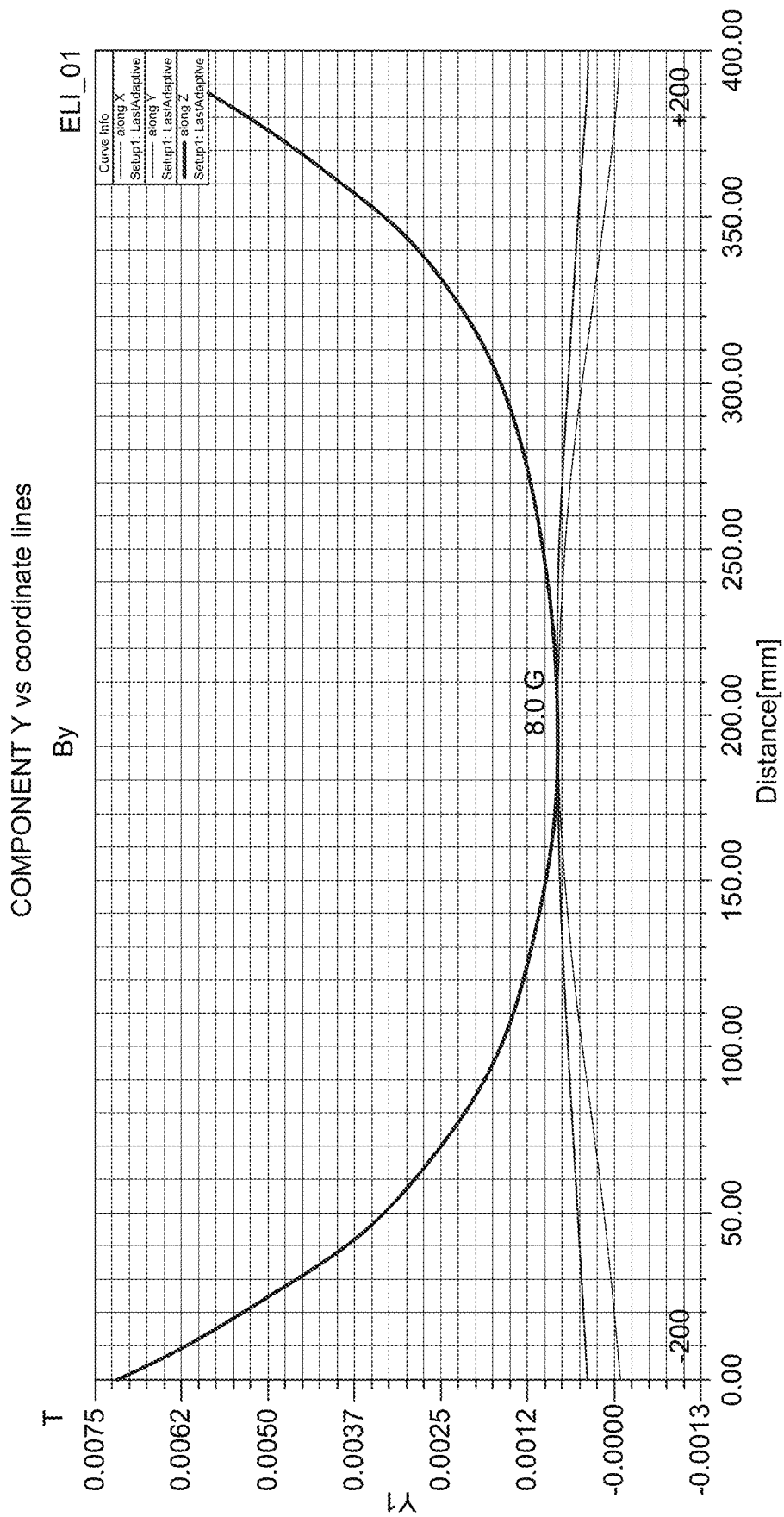
Figure 6E:
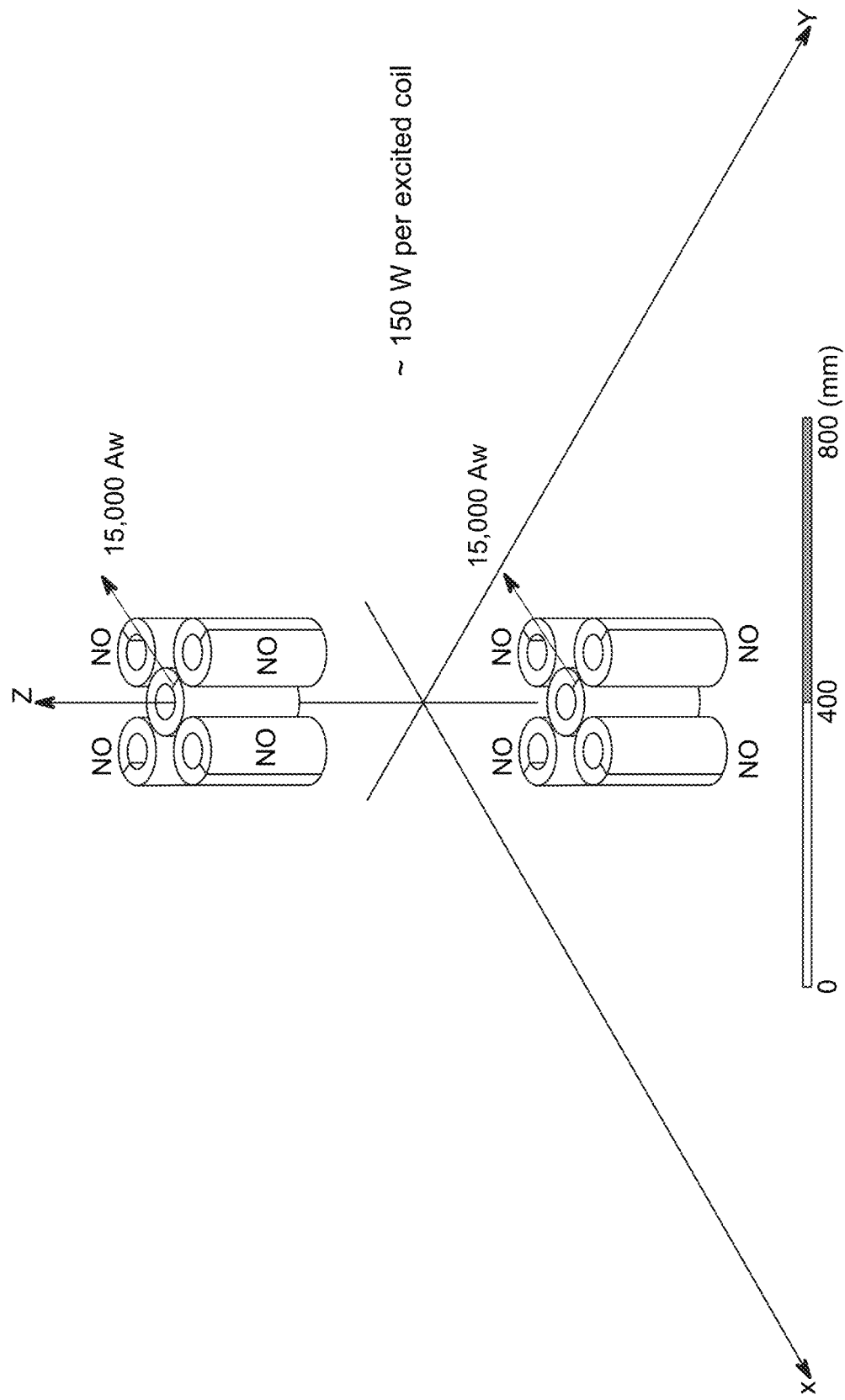
Figure 6F:
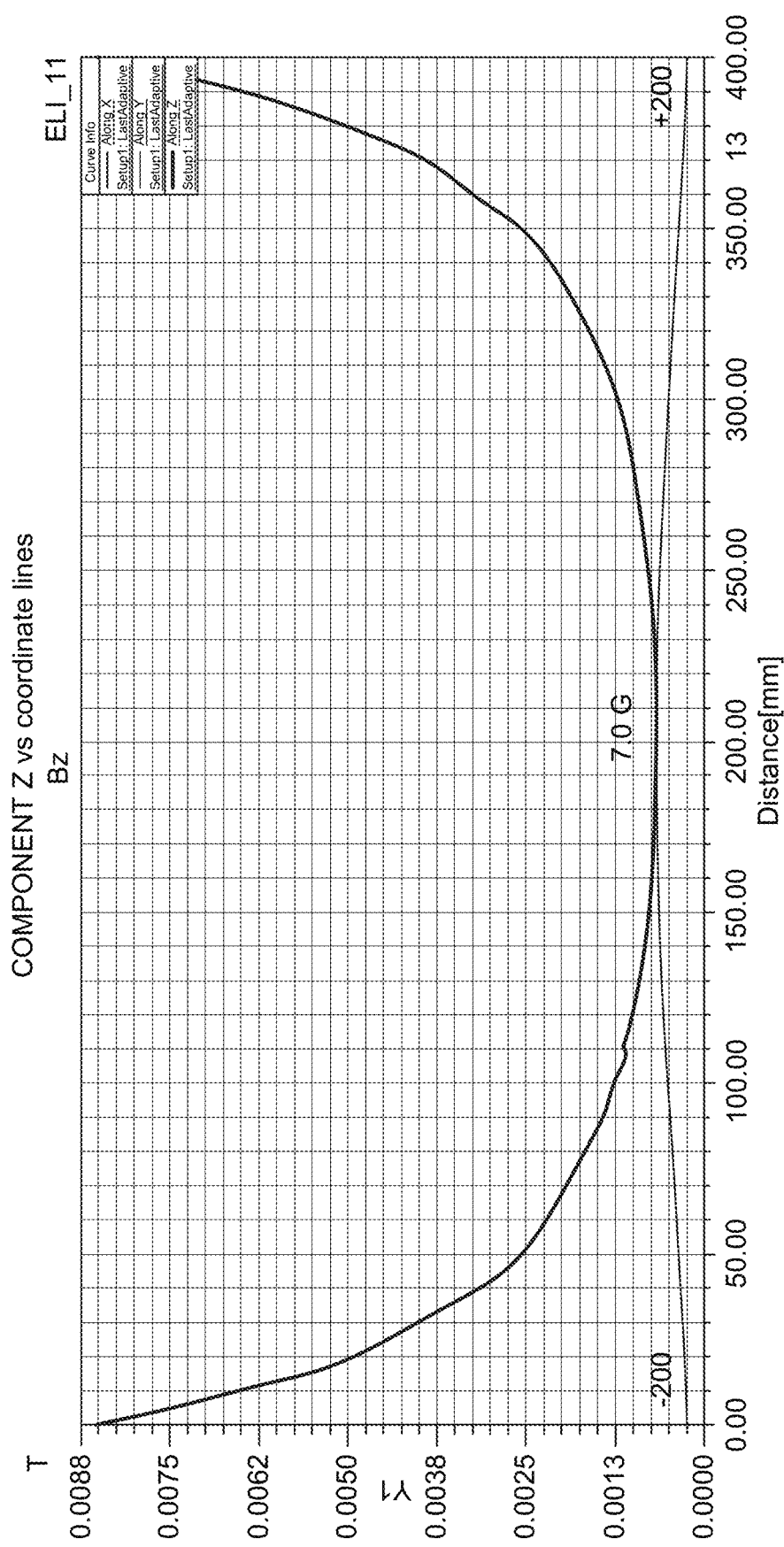
Figure 7A:
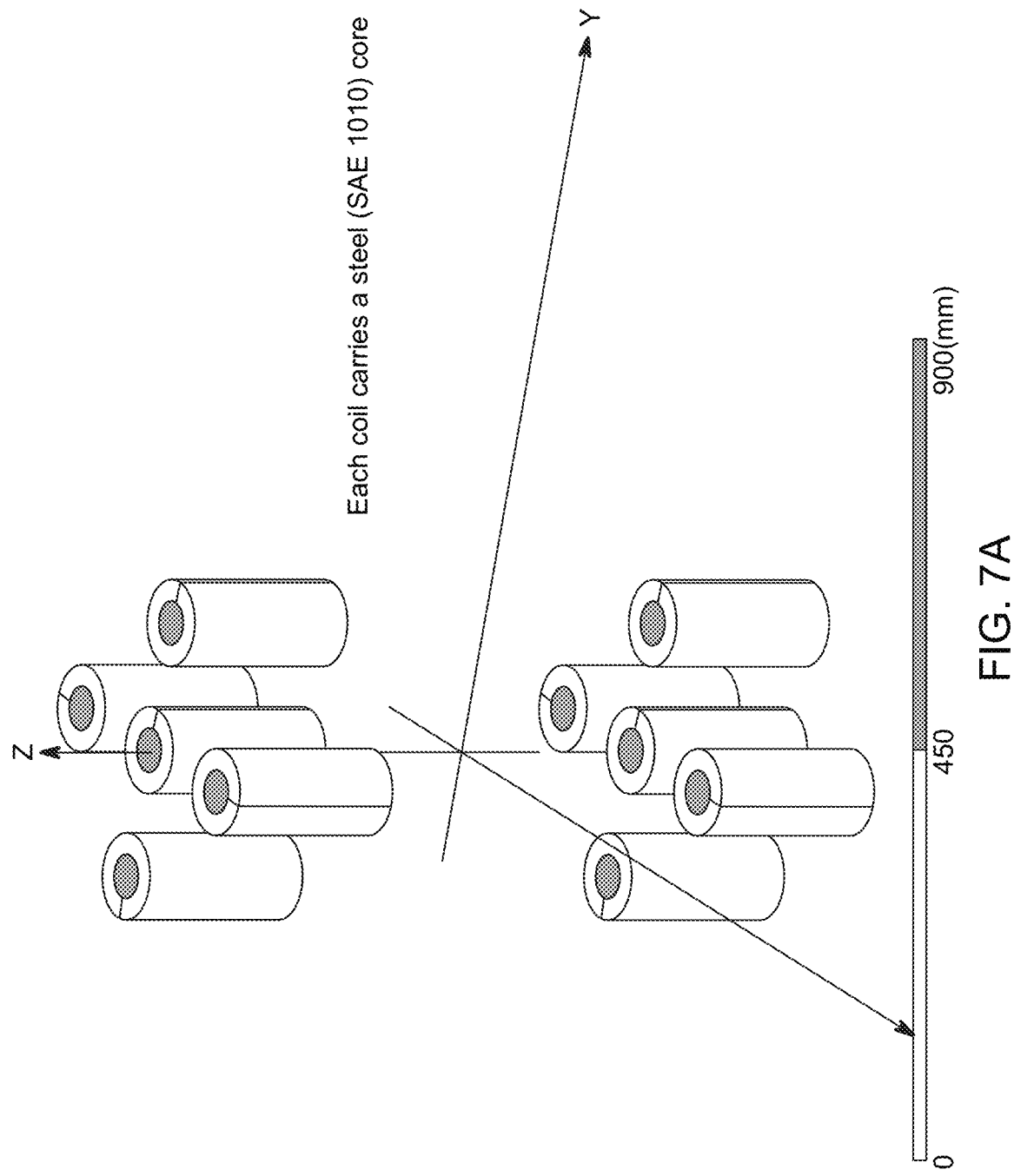
Figure 7B:
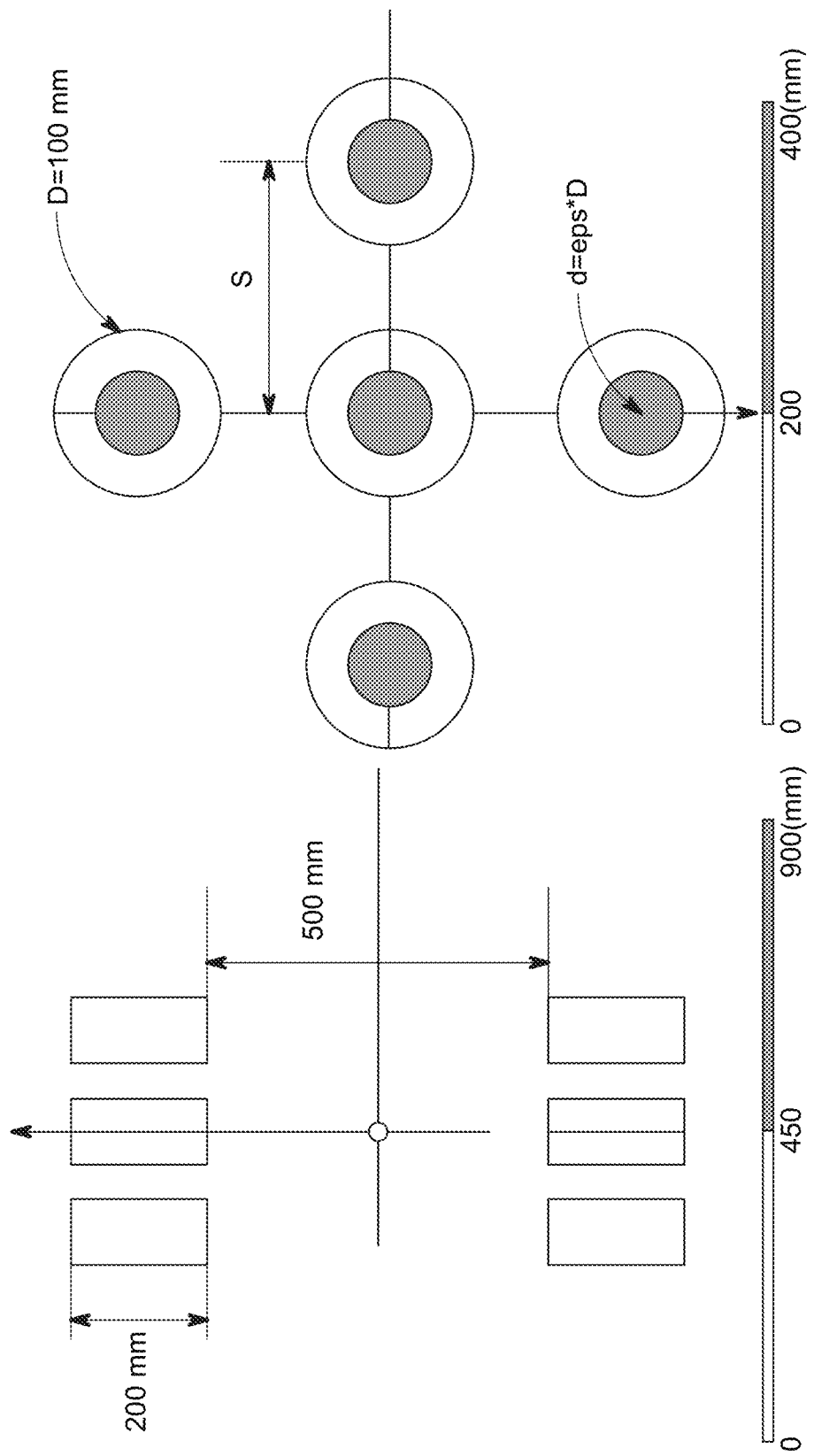
Figure 7C:
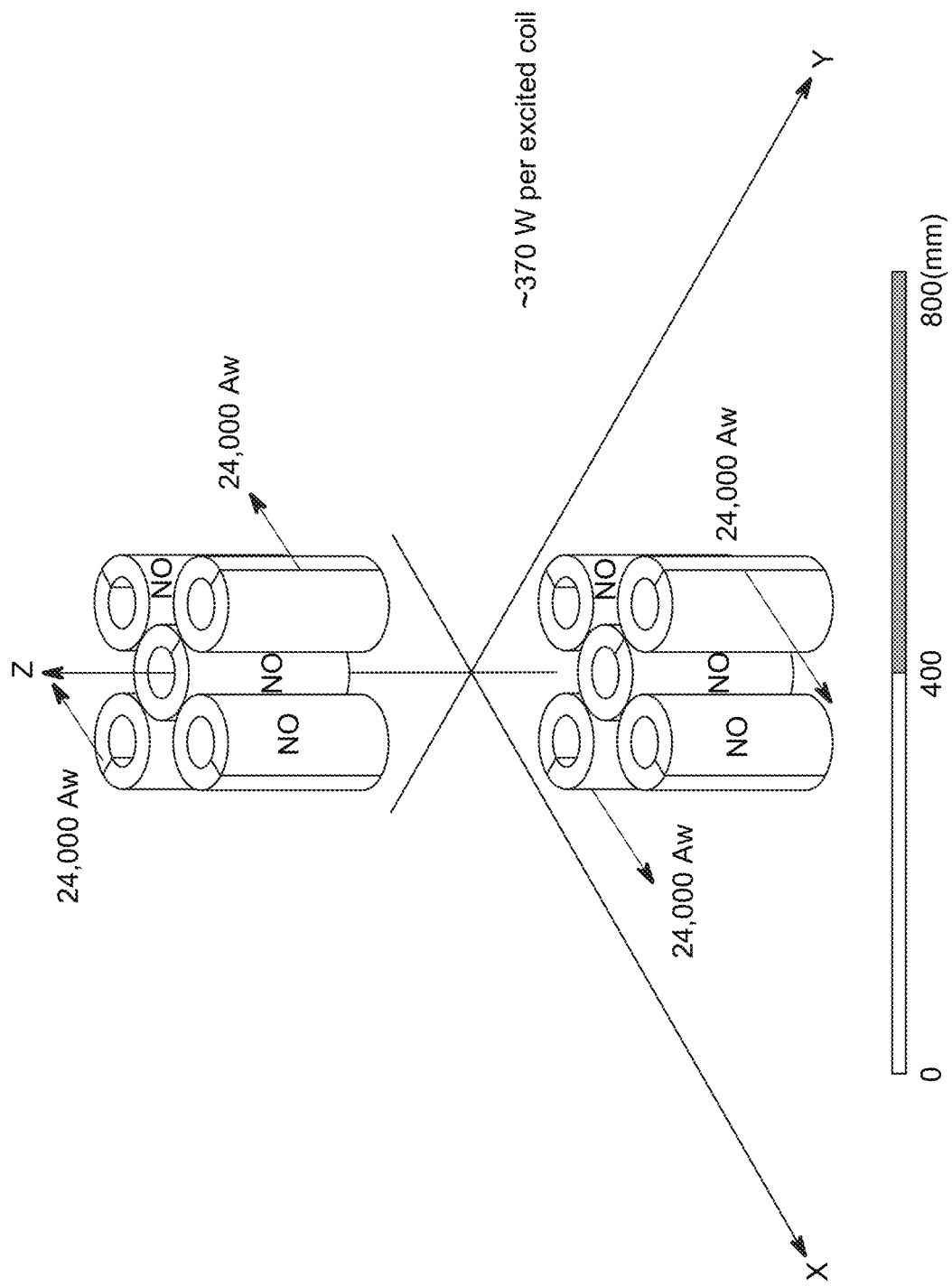
Figure 8A:
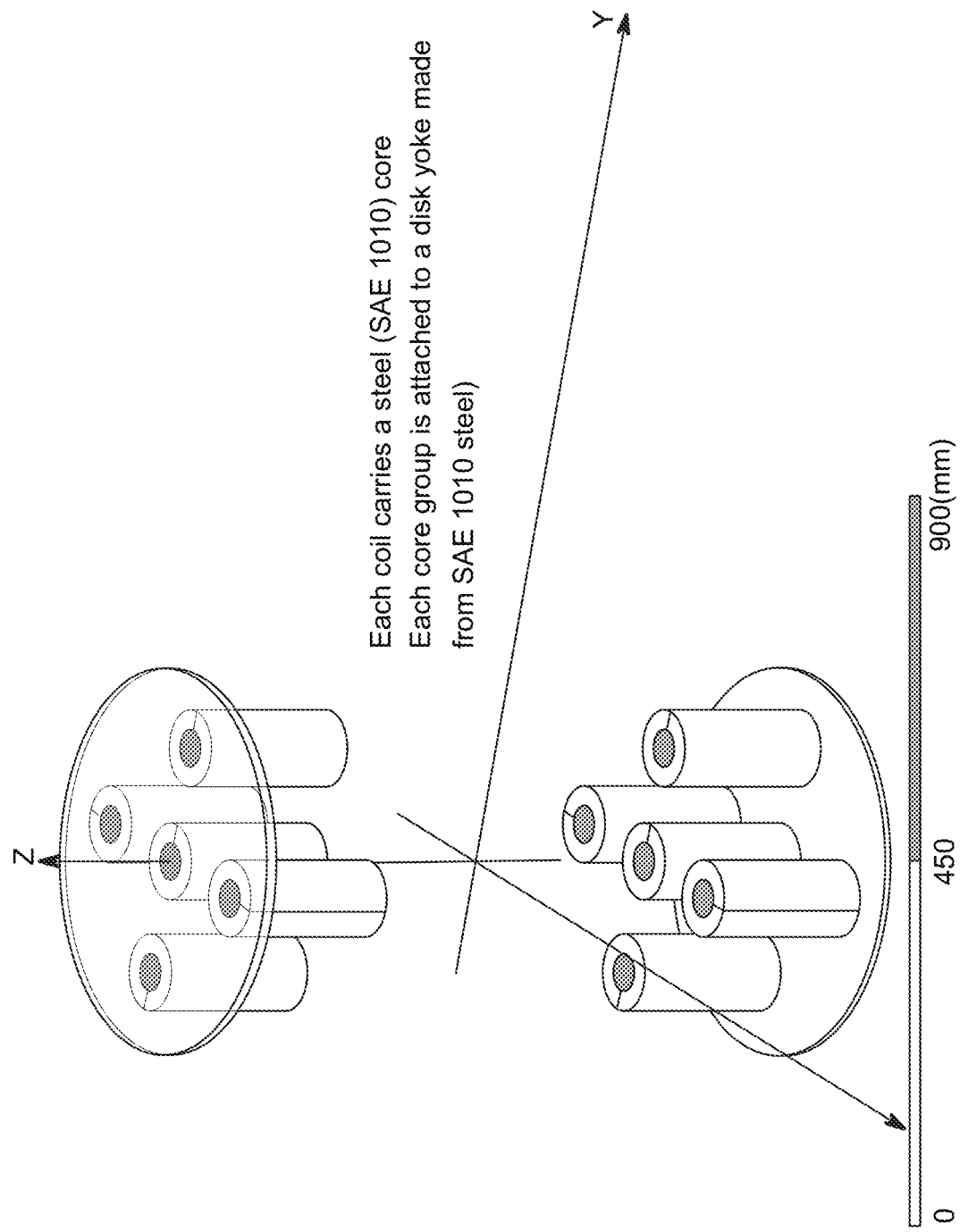
Figure 8B:
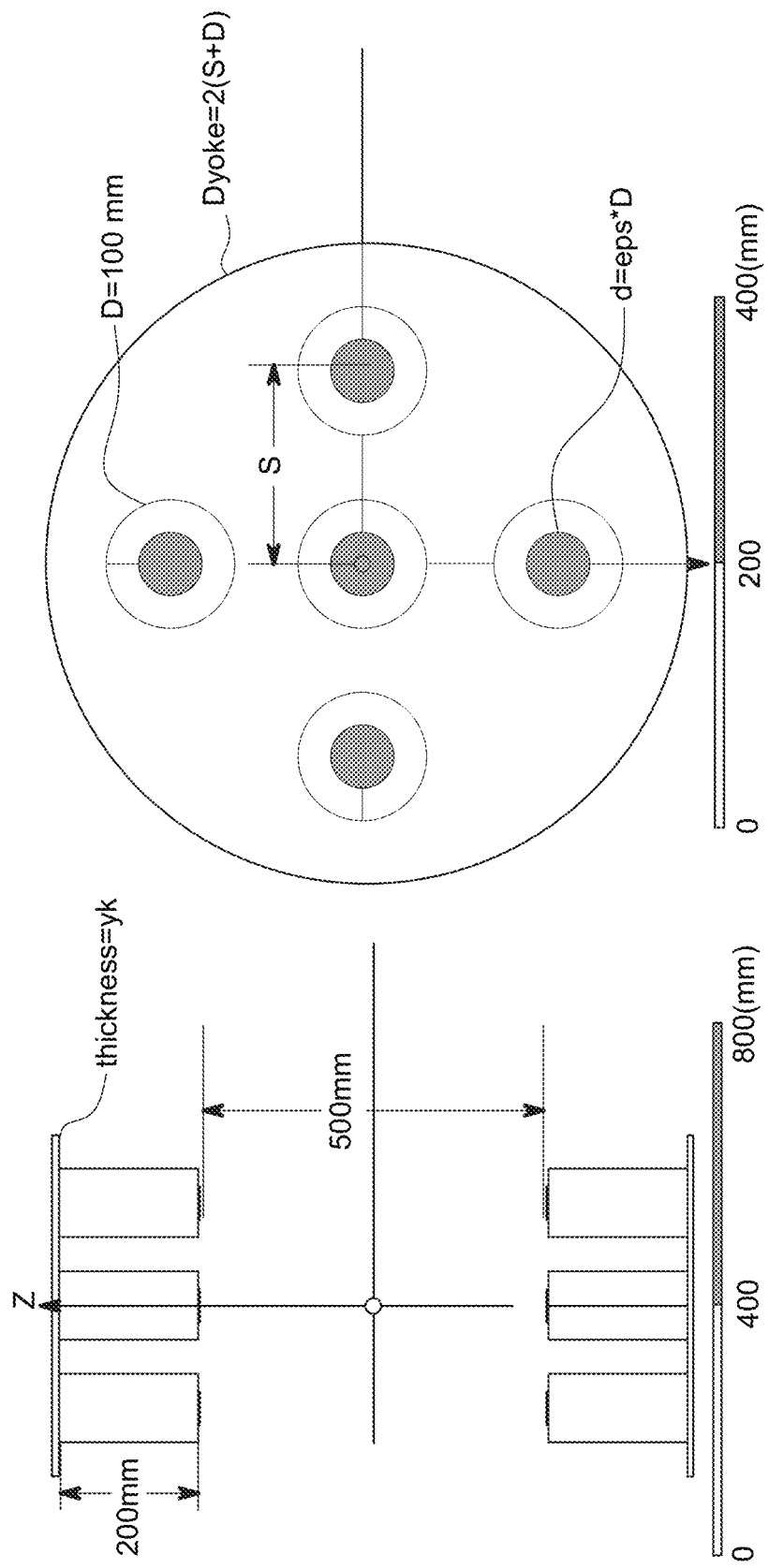

This embodiment utilizes the fact that the lines of a magnetic field generated by a coil form closed loops that extend outside of the coil. Hence, the system is composed of two or more coils located near the operational region, but not enclosing the operational region. The coils are orthogonal to sub-sections of the operational region. The flux lines of different coils generate a combined field vector based on the superposition principle, effectively creating a focus region (or multiple focus regions) in the operational region with stronger or better-controlled magnetic field vector. By independently controlling the current in the coils, it is possible to control the magnetic field generated in diverse locations of the operational region at will, including generation of a rotating field, field gradient, other time-varying pulses. FIG. 6A, FIG. 6B show a diagram of an example of such a setup where 10 parallel coils are located in 2 planes (5 coils in each plane), orthogonal to the operational region which is placed between the planes. It is possible to change this setup, e.g. by adding more coils, changing the orientation of each plane of coils in reference to the operational region, or place the coils in a non-planar configuration (e.g., concentrically facing the operational region). In addition, it is possible to add cores inside the coils to increase the magnetic field (example FIG. 7A, FIG. 7B) or add a yoke outside the coils, again to increase the magnetic field (example FIG. 8A, FIG. 8B). The configuration of the coils, cores and yokes can be altered in space to better control magnetic field distribution. In this setup, we define the variables d, eps, D, S, as specified in FIG. 6B.

For S=100 mm, eps=0.5, FIG. 6C, FIG. 6D, FIG. 6E, FIG. 6F show the results of a finite element simulation demonstrating the ability to accurately generate a desired magnetic field vector in any 3D direction at a central focused point in the operations area, by independently controlling each of the coils, including shutting down some of the coils, applying different levels of current in different directions.

Figure 6G:
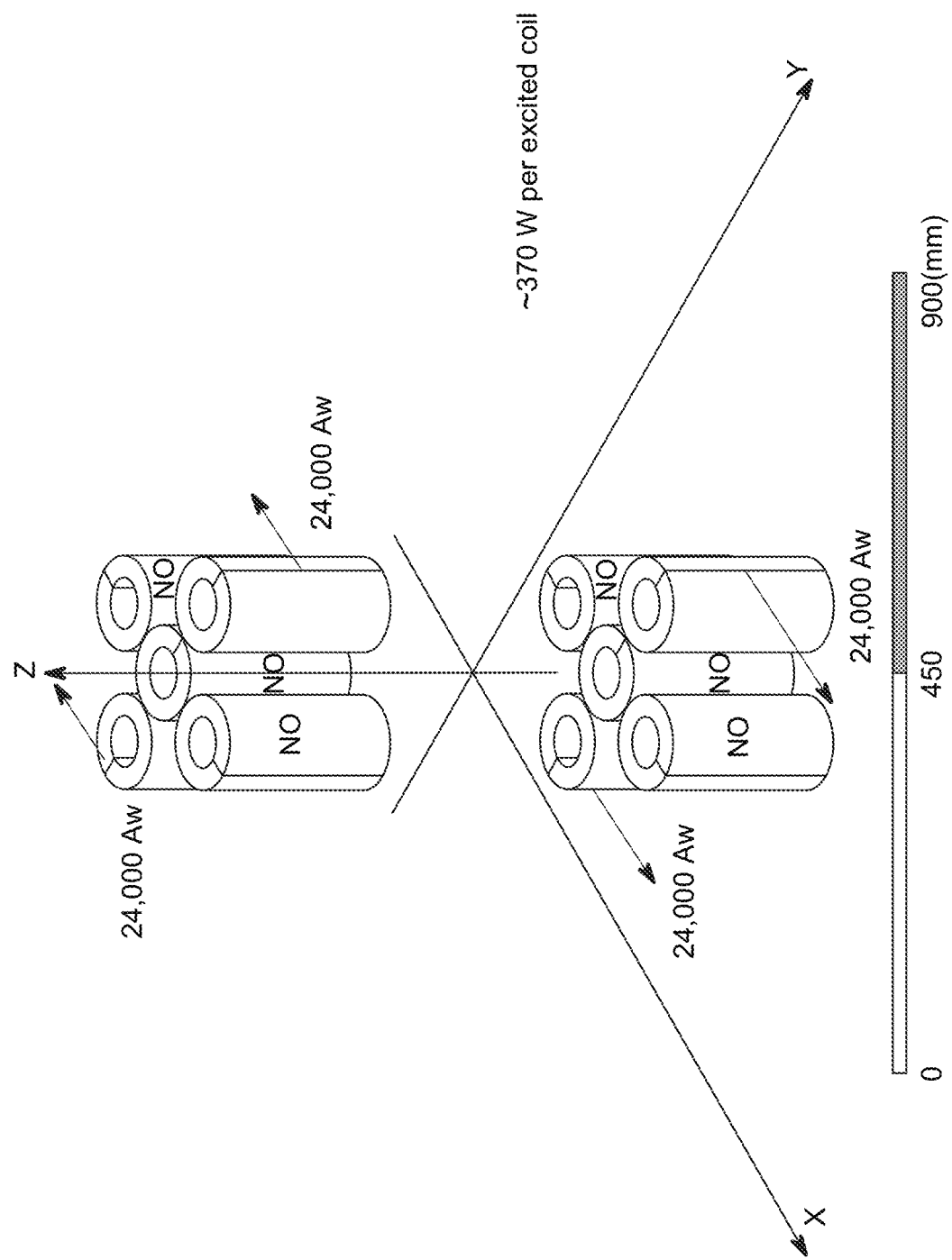
Figure 6H:
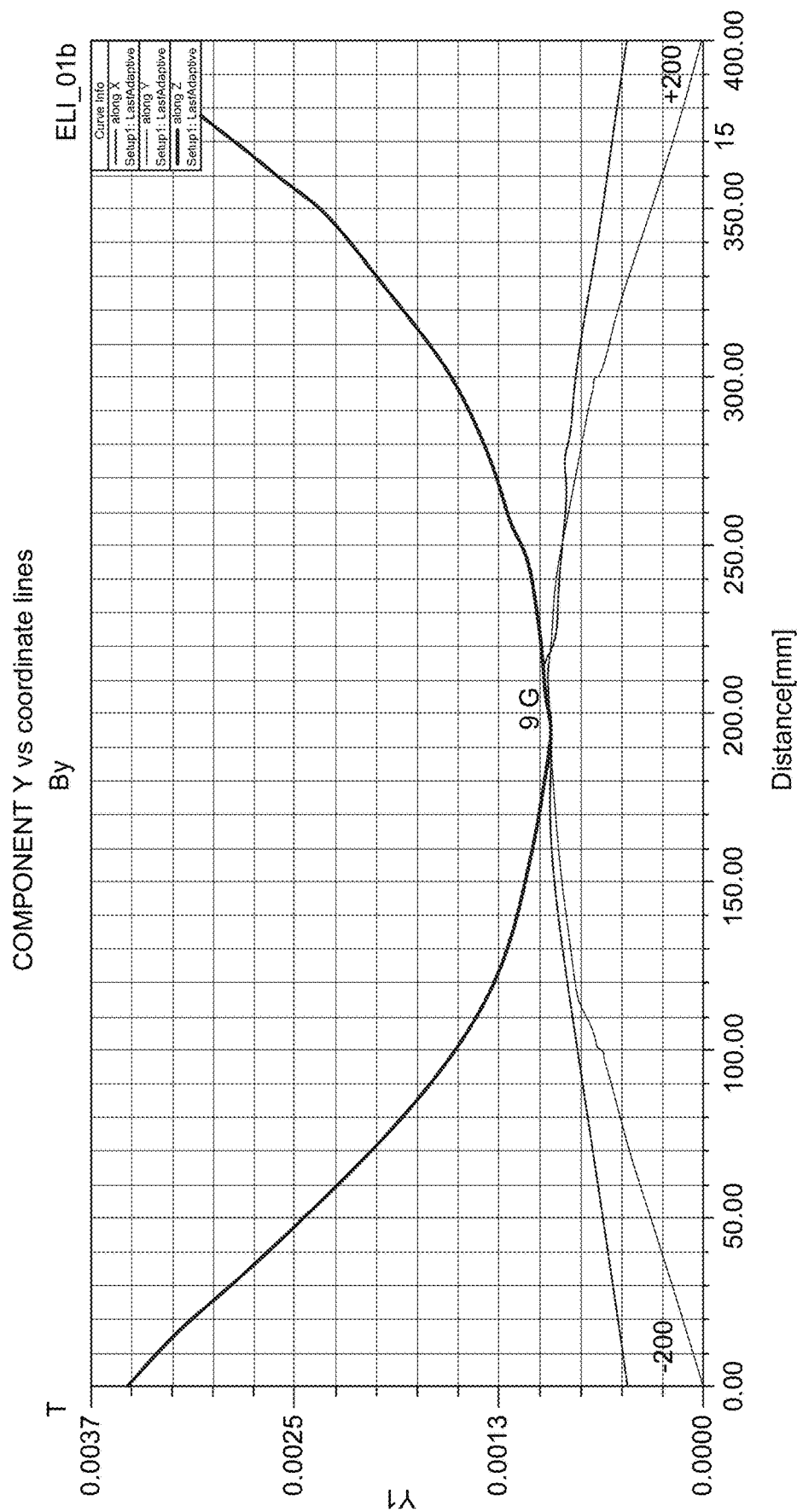

FIG. 6G, FIG. 6H show that by increasing the parameter S to 200 (better spread coils), it is possible increase the magnitude of magnetic field by >25%.

FIG. 7C, FIG. 7D, FIG. 7E, FIG. 7F show the ability to amplify the magnetic field by 4-5 times, using the addition of a SAE 1010 steel core.

Figure 7D:
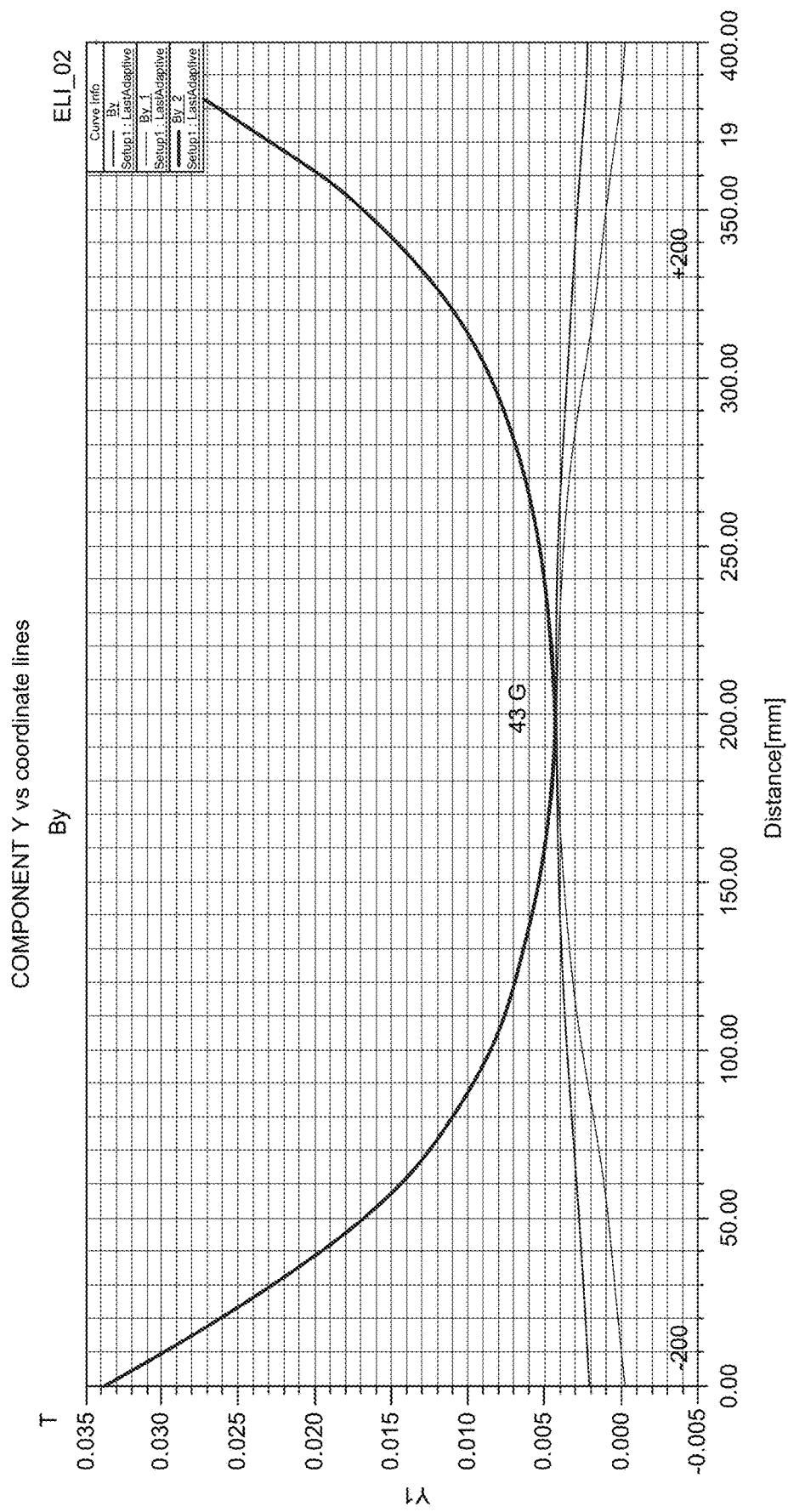
Figure 7E:
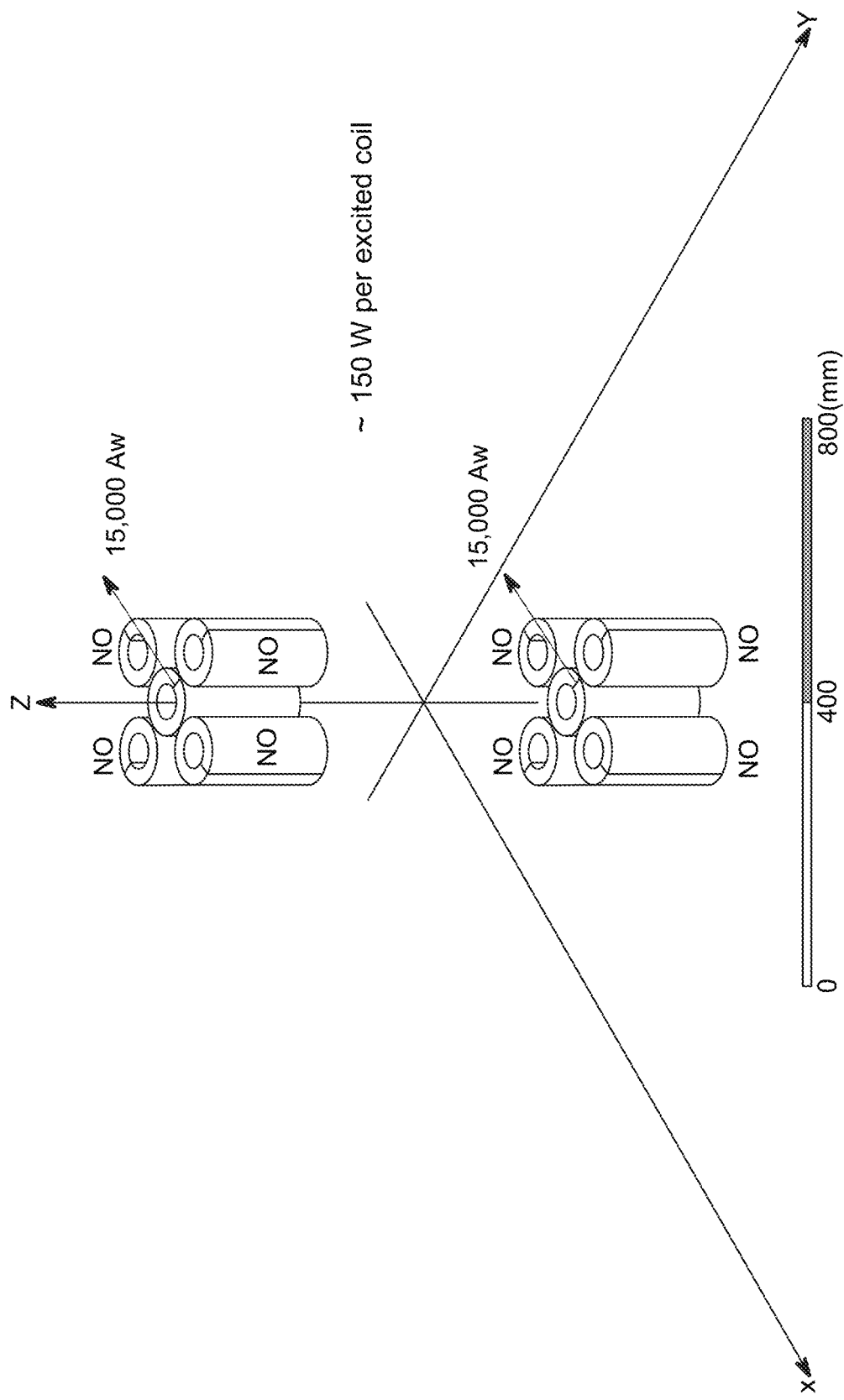
Figure 7F:
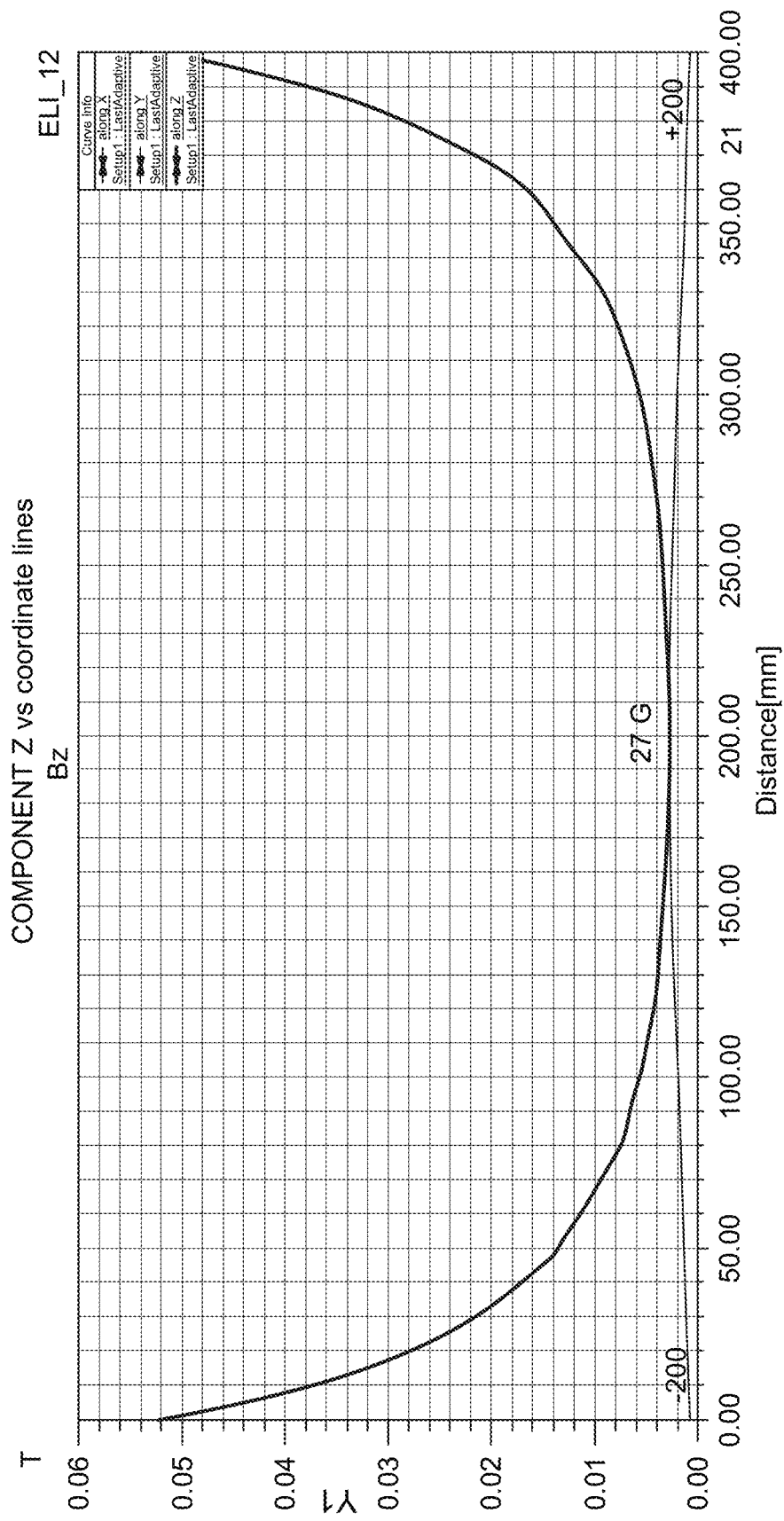
Figure 8C:
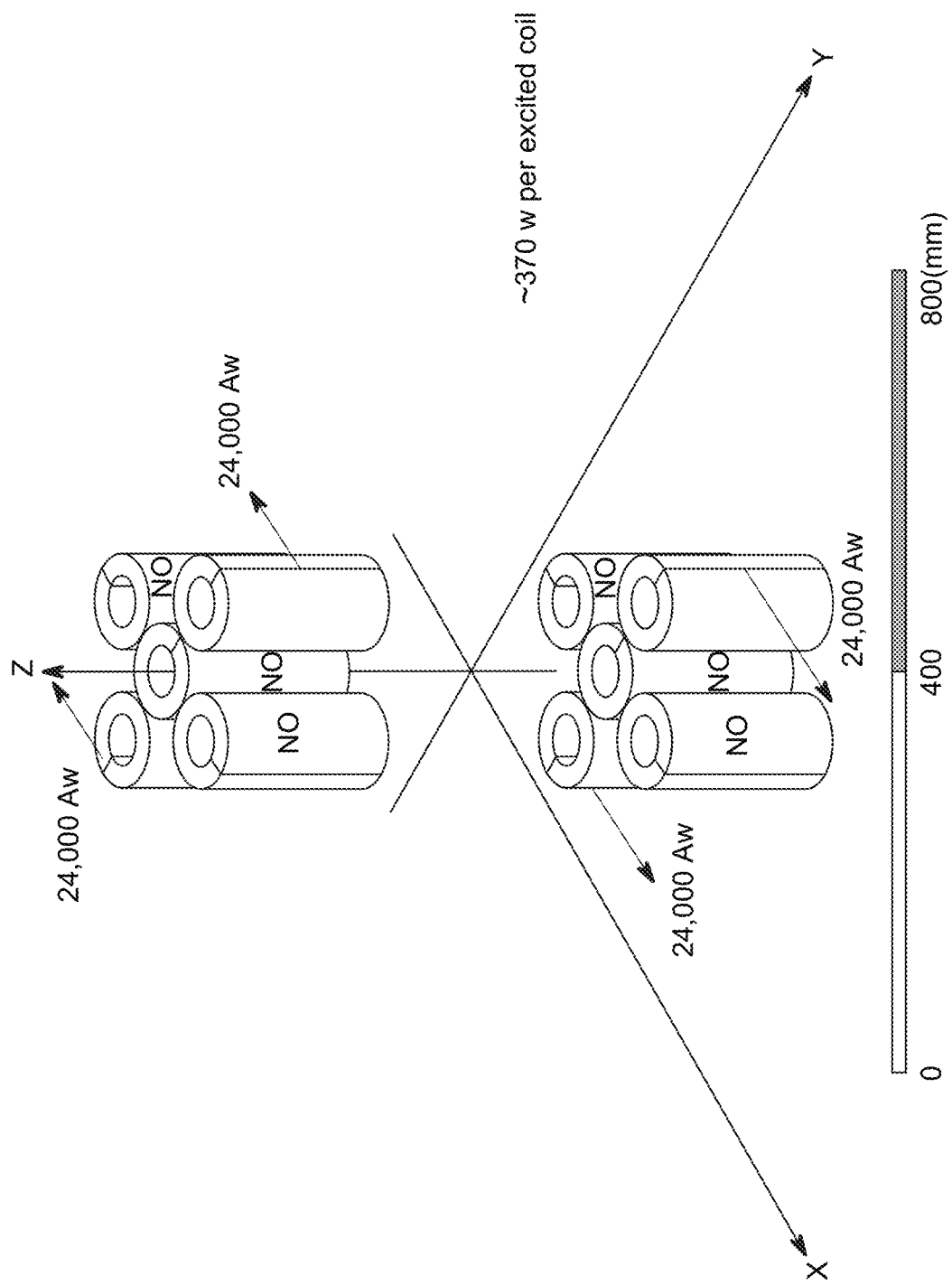
Figure 8D:
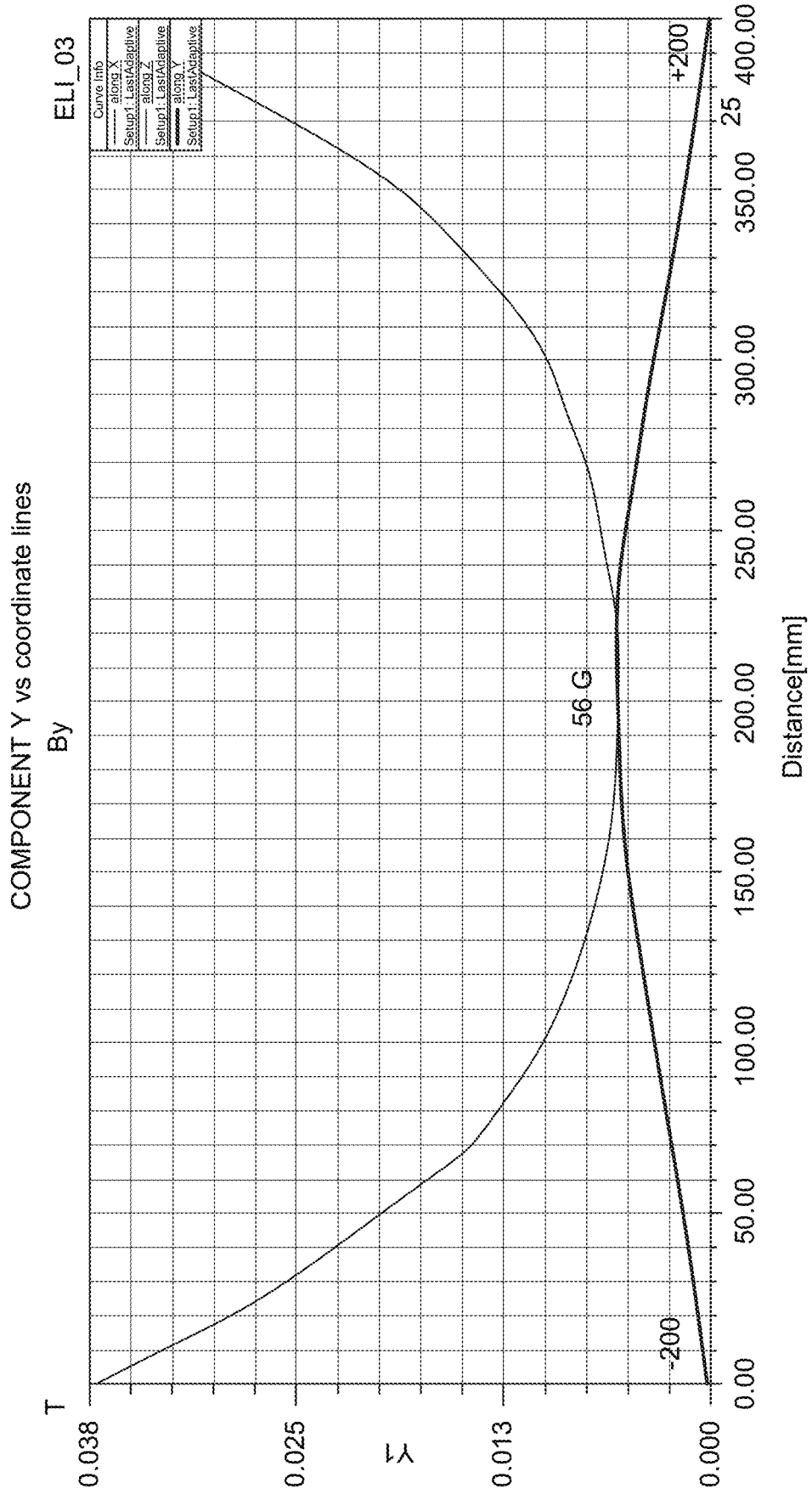

FIG. 8C, FIG. 8D show the ability to increase the magnetic field by approximately 30%, using the addition of a SAE 1010 steel yoke of 10 mm width, radius (S+D) in addition to the core (compare FIG. 8D to FIG. 7D).

Figure 8E:
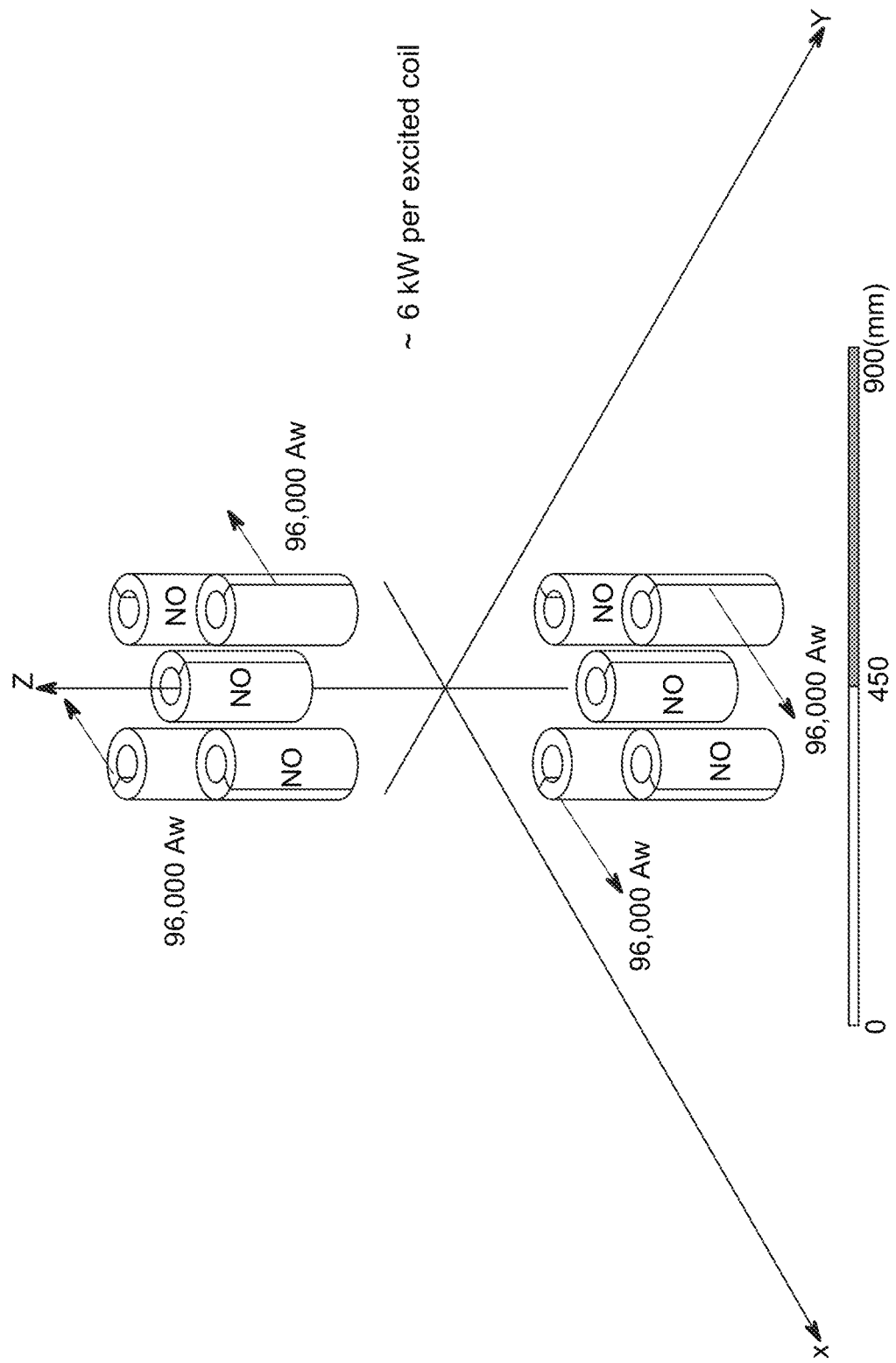
Figure 8F:
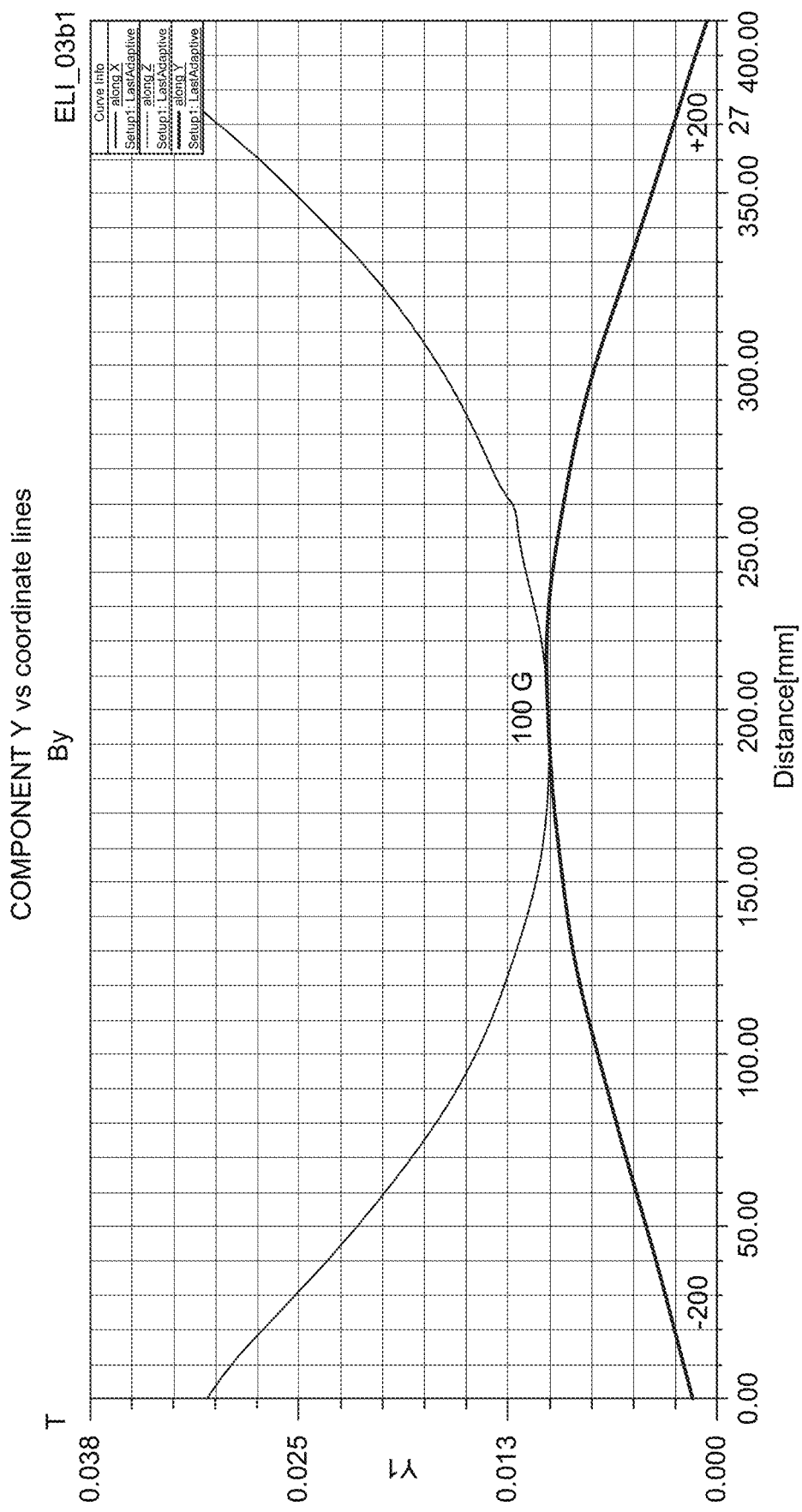

FIG. 8E, FIG. 8F demonstrate a field of 100 Gauss in the focus region with a system with parameter S=200 mm, higher current, a yoke and cores.

The latter suboptimal configuration allows generation of controllable, arbitrary magnetic field vectors in various areas of the operational region, while generating 24 kW of heat, allowing for commercially available, compact water cooling. Furthermore, such a system is weight-efficient, with weight of approximately 250 kg without specific weight optimization, making it a practical solution for a medical setting in light of the restrictions listed above.

Also, in this system it is possible to generate a controllable magnetic field of any direction/amplitude, as needed for remote power transfer, communication, or propulsion of the internal device.

Compound Hallbach Coil System

There are two subsystems: the first generates a magnetic field in the xy-plane; the second generates a magnetic field in the z-direction.

The first subsystem is composed of two distributed Halbach arrays of identical round rod-like permanent magnets (around the z-axis). The second subsystem is a solenoidal coil wound around the z-axis wrapping the above permanent magnet array.

Both subsystems may further be augmented by a thin cylindrical (around z-axis) ferromagnetic shell.

The magnets incorporated in the first system above are configured to synchronously rotate around their axis.

The number of rod-like permanent magnets and their size can be adjusted to change the field strength, or the system size.

The magnets do not have to be rod-shaped, and may have different geometries as desired.

Multiple concentric layers of such rod-like magnets can be placed in the system (one layer of rods over another layer), for generating even stronger fields, with greater control over amplitude and generation of more uniform fields.

The drawings show a representative example of such a system, for a single layer of 48 rod-like magnets.

Subsystem to Generate a Field in the xy-Plane

Figure 9:
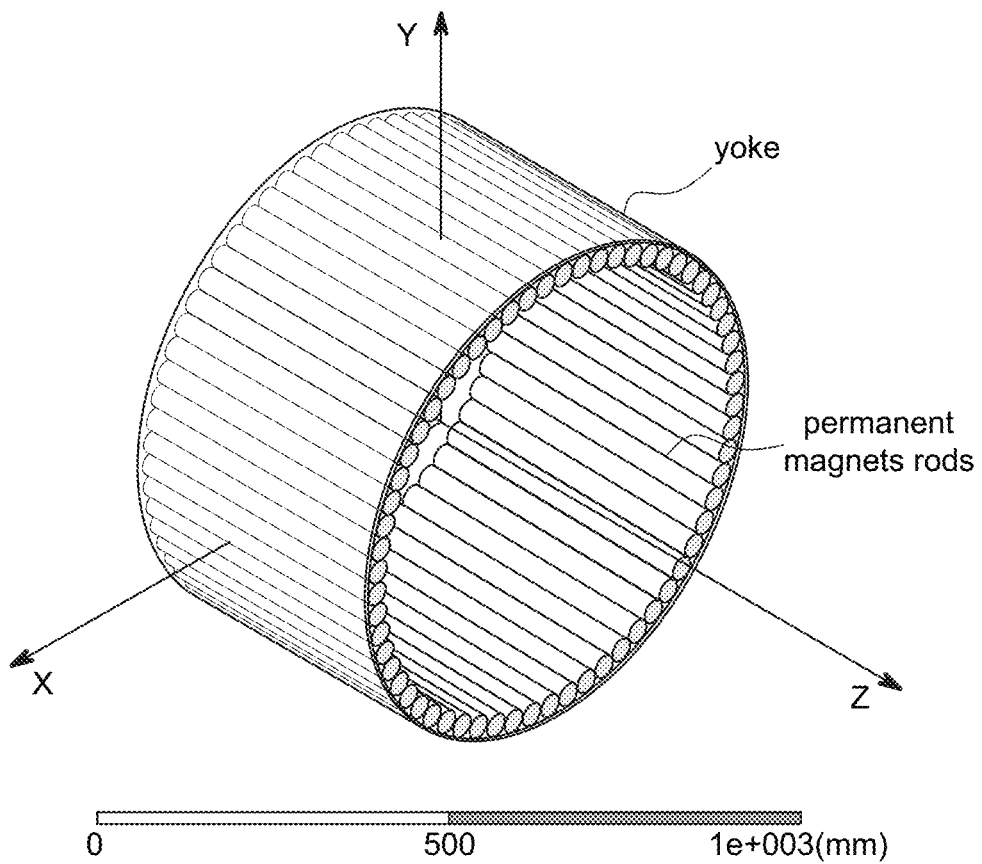

FIG. 9 illustrates a non-limiting example of a sub-system implemented as single-layer array of 48 annually distributed radially magnetized identical permanent magnet rods surrounded by a thin ferromagnetic shell playing a role of yoke.

Figure 10:
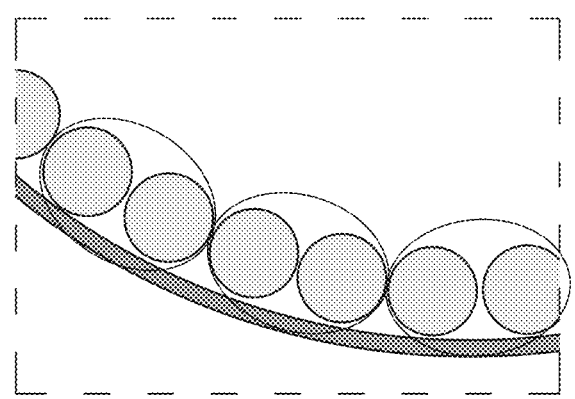

Each rod is configured to rotate around its axis (e.g. being driven by a small stepper motor). The magnets are grouped into couples (FIG. 10).

Figure 11A:
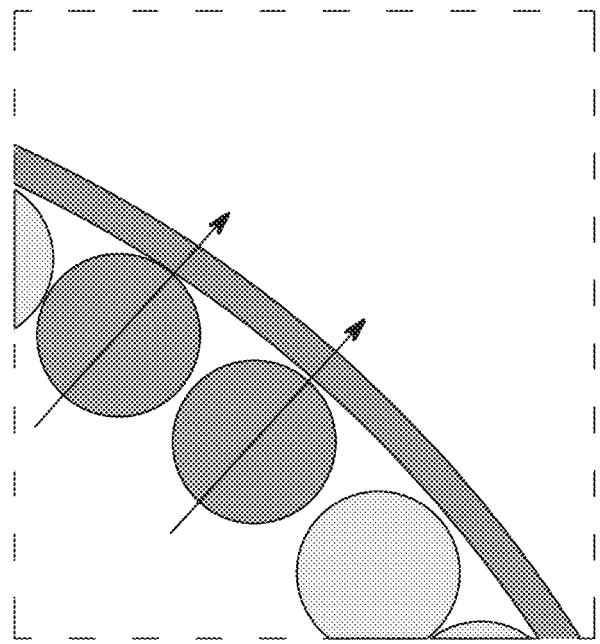
Figure 11B:
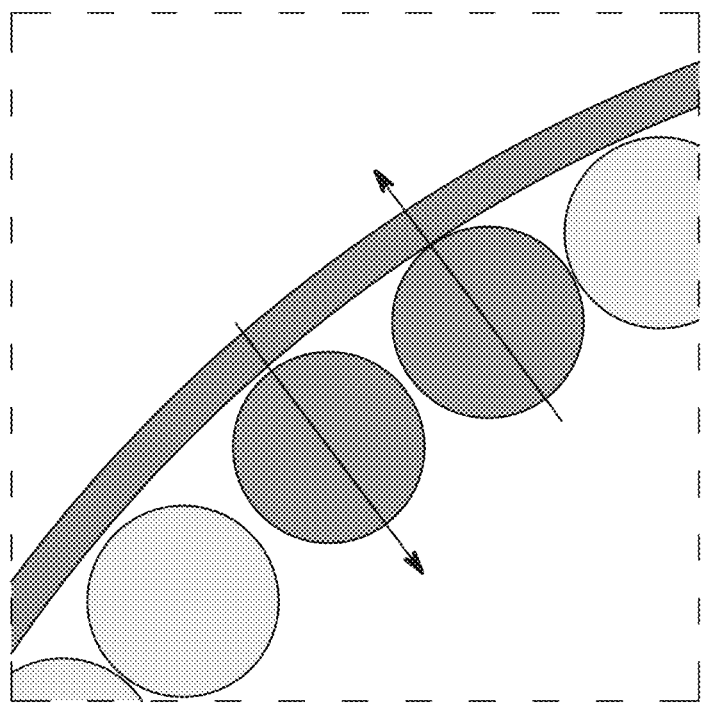

In order to generate maximal field, the coupled magnets are oriented co-directionally (FIG. 11A); in order to generate zero-field, they are oriented counter directionally (FIG. 11 B). The average magnetization vectors of couples are distributed per the Halbach approach.

Figure 12:
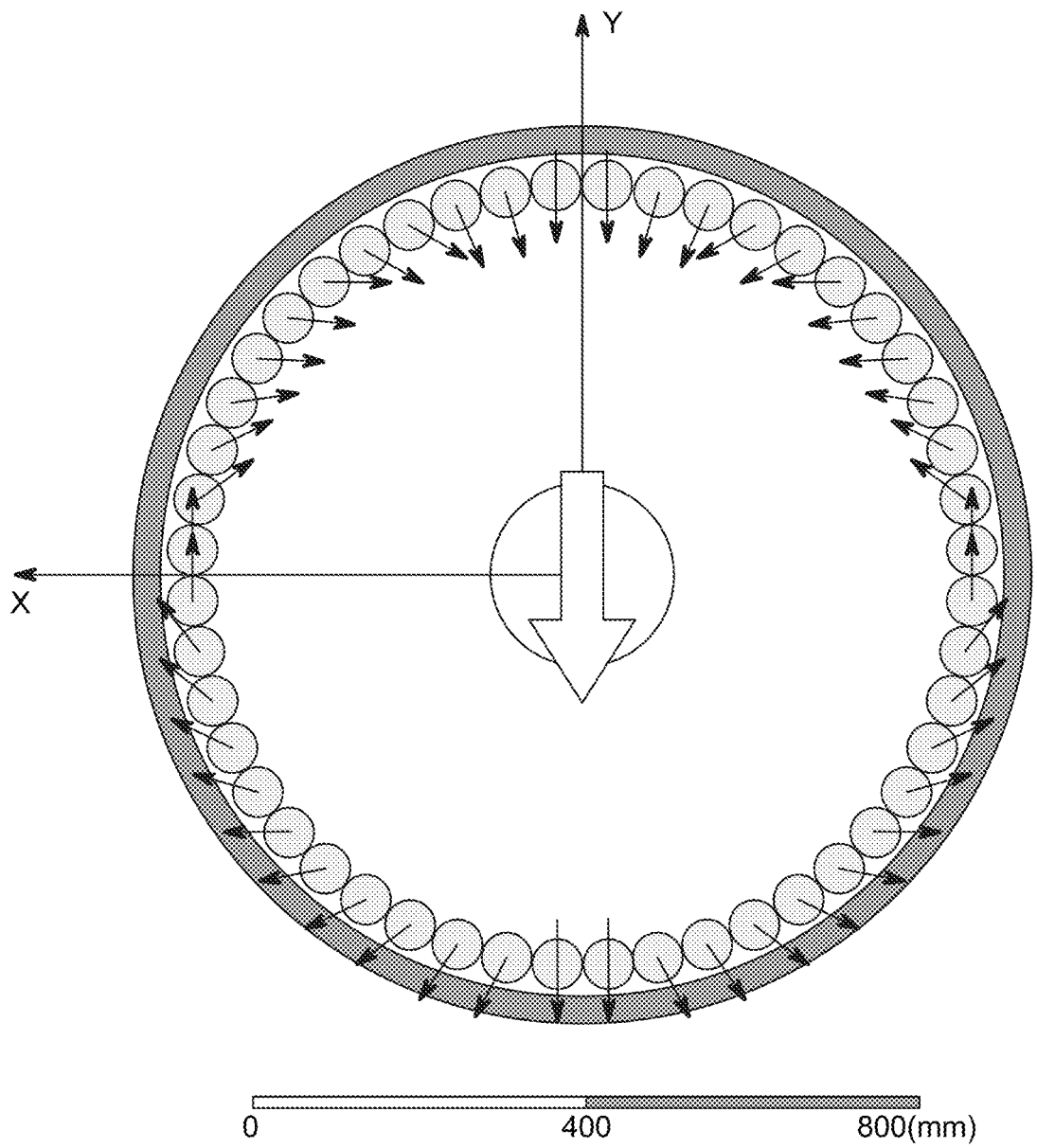

FIG. 12 shows the magnets' orientation generating maximal y-directed magnetic field.

Figure 13:
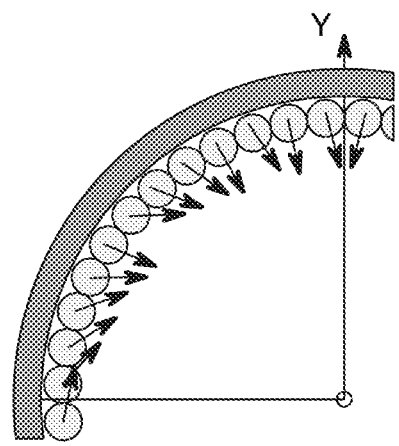

FIG. 13 shows an example of the magnet orientation for generating ay-directed magnetic field of a smaller magnitude. The rods within each couple are tilted relative to their nominal direction. In order to rotate the field in the xy plane at a definite rotating speed, for example, at 20 Hz then all the rods are rotated at angular speed 20 Hz=1,200 rpm which is easily implemented, e.g. by using a direct drive stepper motor. The rods may be driven either individually or may be mechanically connected together (e.g., by a belt).

Figure 14:
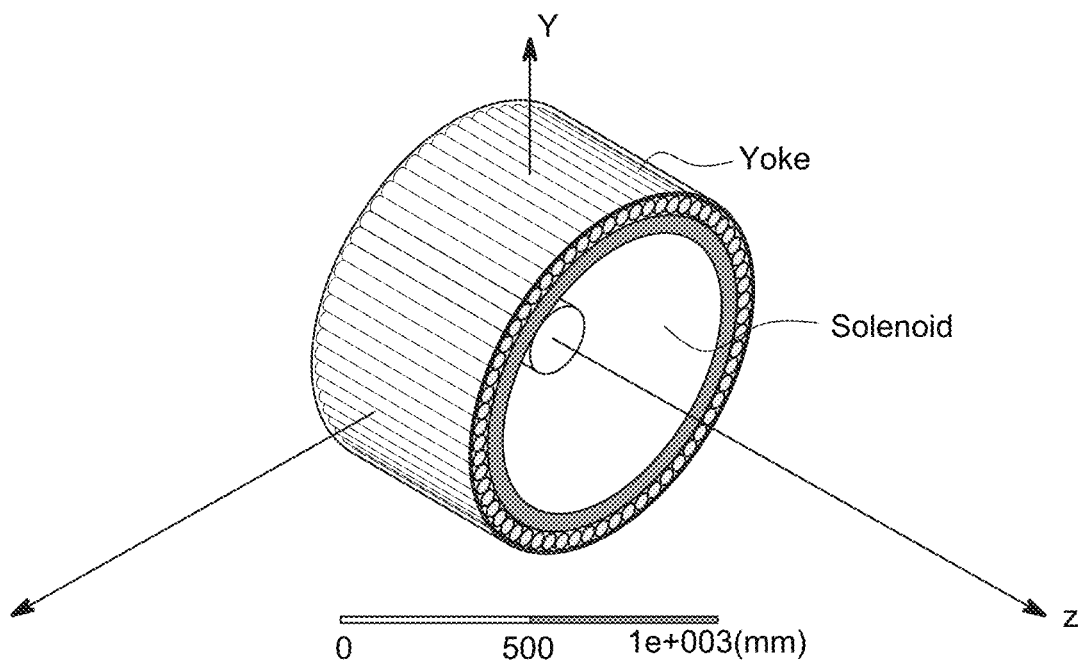

FIG. 14 shows an entire system according to an embodiment of the invention, which includes the first subsystem shown in FIG. 9 and the second subsystem based on a concentric solenoid. In order to enhance the z-magnetic field, a ferromagnetic shell-like yoke is used. In this system, the current in the z-axis coil is modulated as needed, generating a fixed field, gradient, or any other time-varying pulses, at a wide frequency range (from Hz to GHz). This allows using the z-axis for remote power transfer or communication with the internal device, per the requirements previously set forth.

A goal is to ensure proper spatial alignment of the sensory mechanism inside the internal device with the z-axis field component. For example, such a component may be a micro Hall sensor (a communication sensor) or a micro-coil to pick up changes in magnetic flux and convert them to voltage (for energy conversion). If this micro-component is orthogonal to the z-axis, it will not pick up the signal transmitted by the z-axis coil. Thus, according to a related embodiment, three such micro-components (e.g., Hall sensors or micro-coils) are placed orthogonally to one another in the internal device, and are connected to a signal integration/summation circuit in the internal device. Thus, regardless of the orientation of the internal device relative to the z-component of the magnetic field, the entire z-component will be picked up collectively by the three micro-components according to each projection of the z-component thereon. Then, all micro-components' interactions will be aggregated for further processing by the internal device, without loss.

Figure 15:
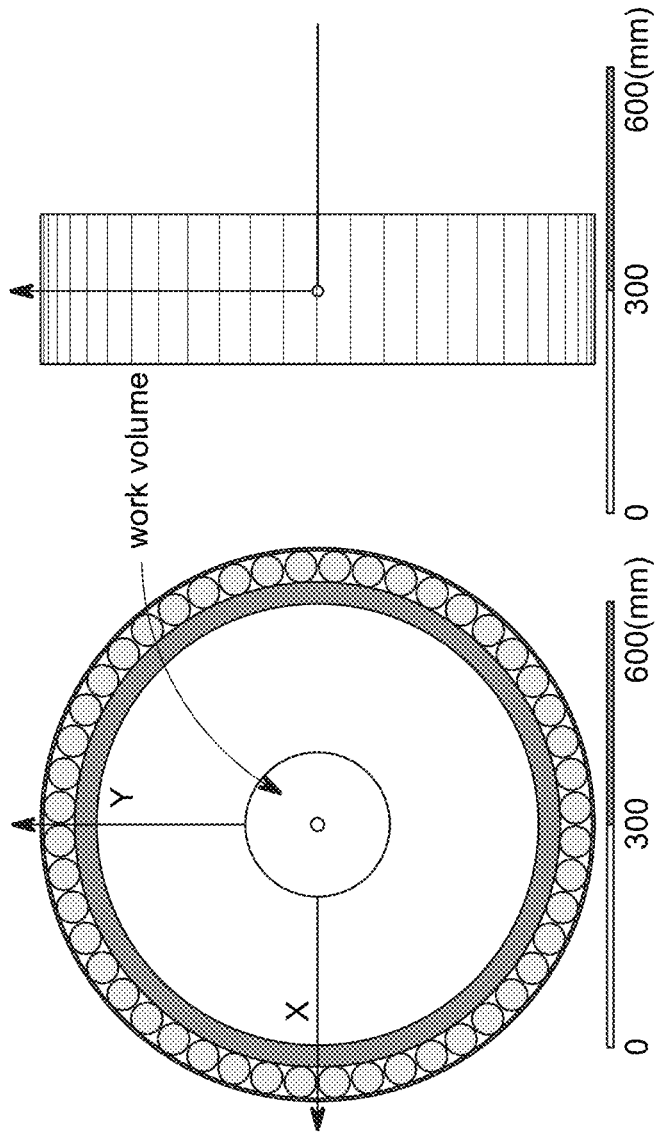
Figure 16:
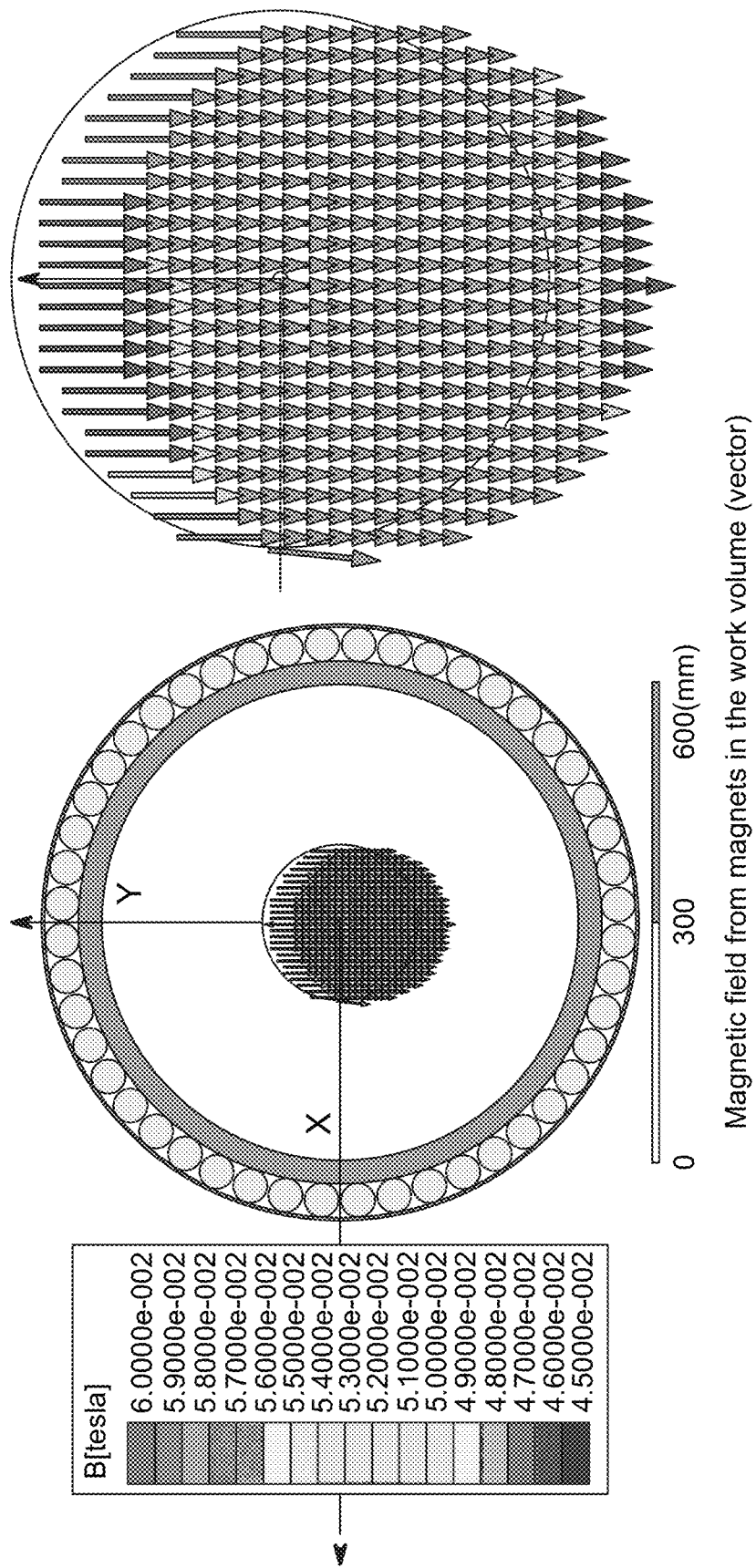

FIG. 15 shows the simulated system having Dia 600 mm opening of the operational region; the length is 200 mm. The magnet rods of 21 mm diameter are made from grade N50M. The yoke shell is made from 3 mm 1020 steel. The coil is wound from Al wire with filling factor 0.45. The simulated vector field in the work volume when the rods in groups are oriented to generate a maximal magnitude (as illustrated in FIG. 12) is shown in FIG. 16.

Figure 17:
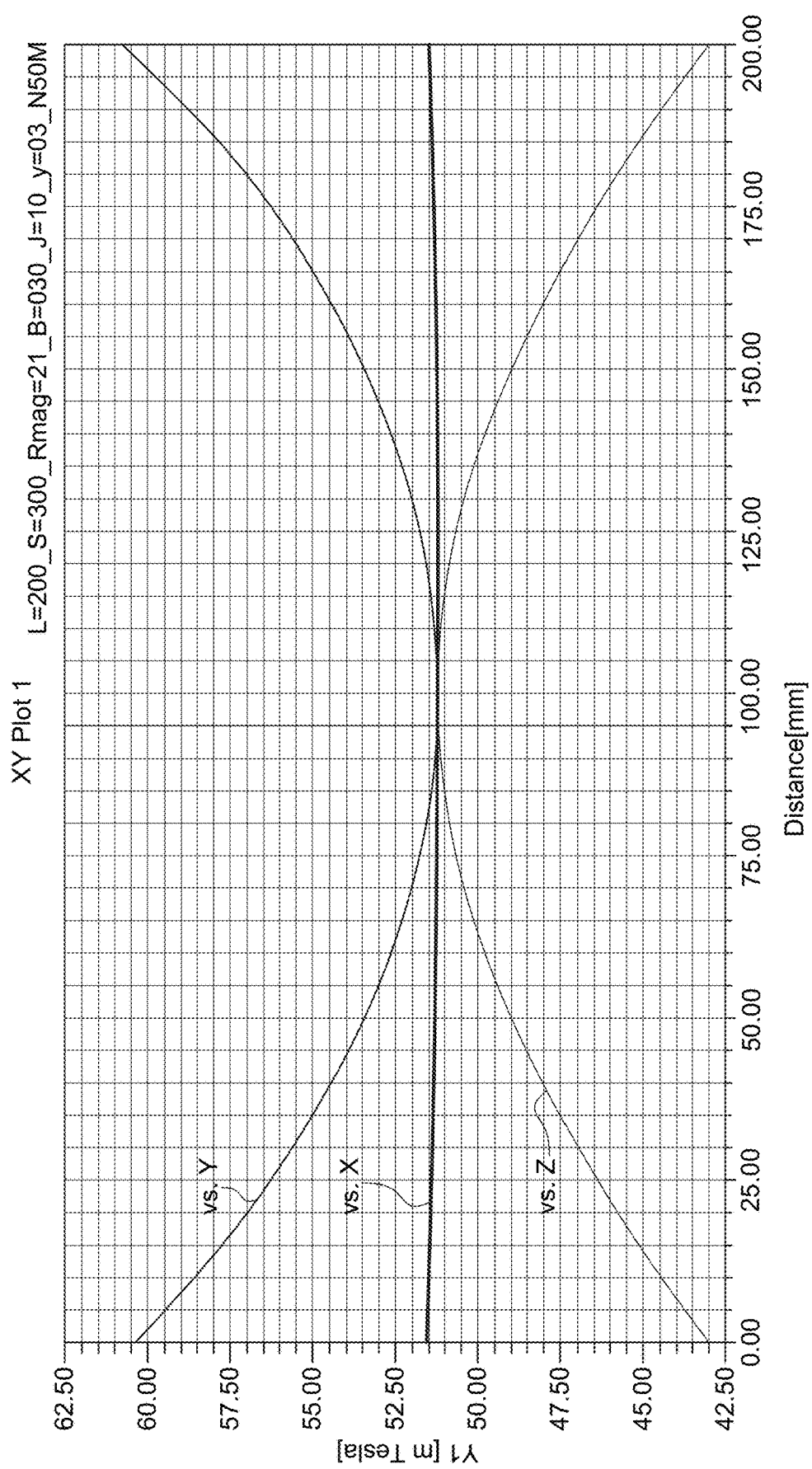

FIG. 17 shows dependences of the field amplitude in the work volume vs. coordinates.

Figure 18:
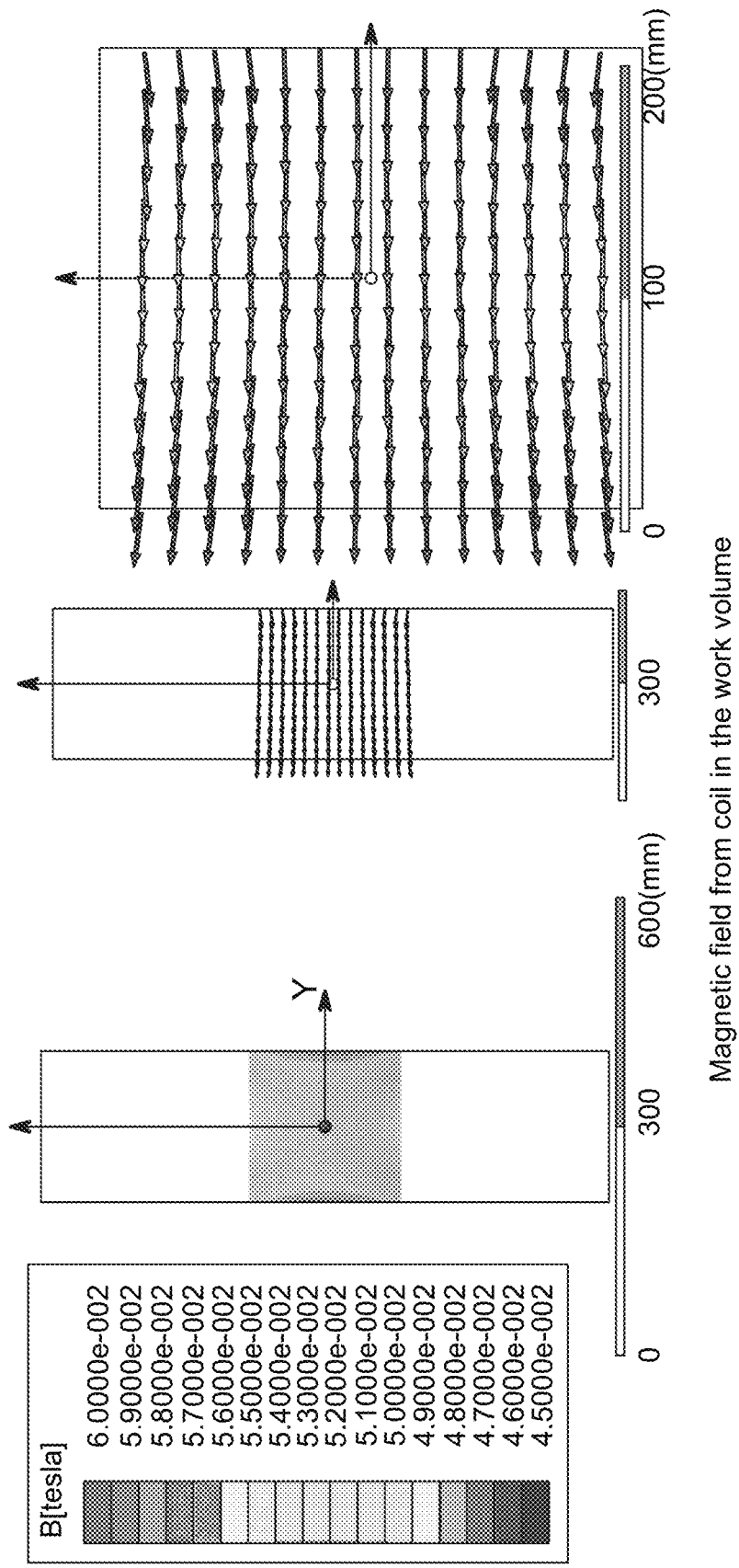

Final Characteristics and Conclusions:

FIG. 18 shows result of simulating filed from the coil in the work volume.

Figure 19:
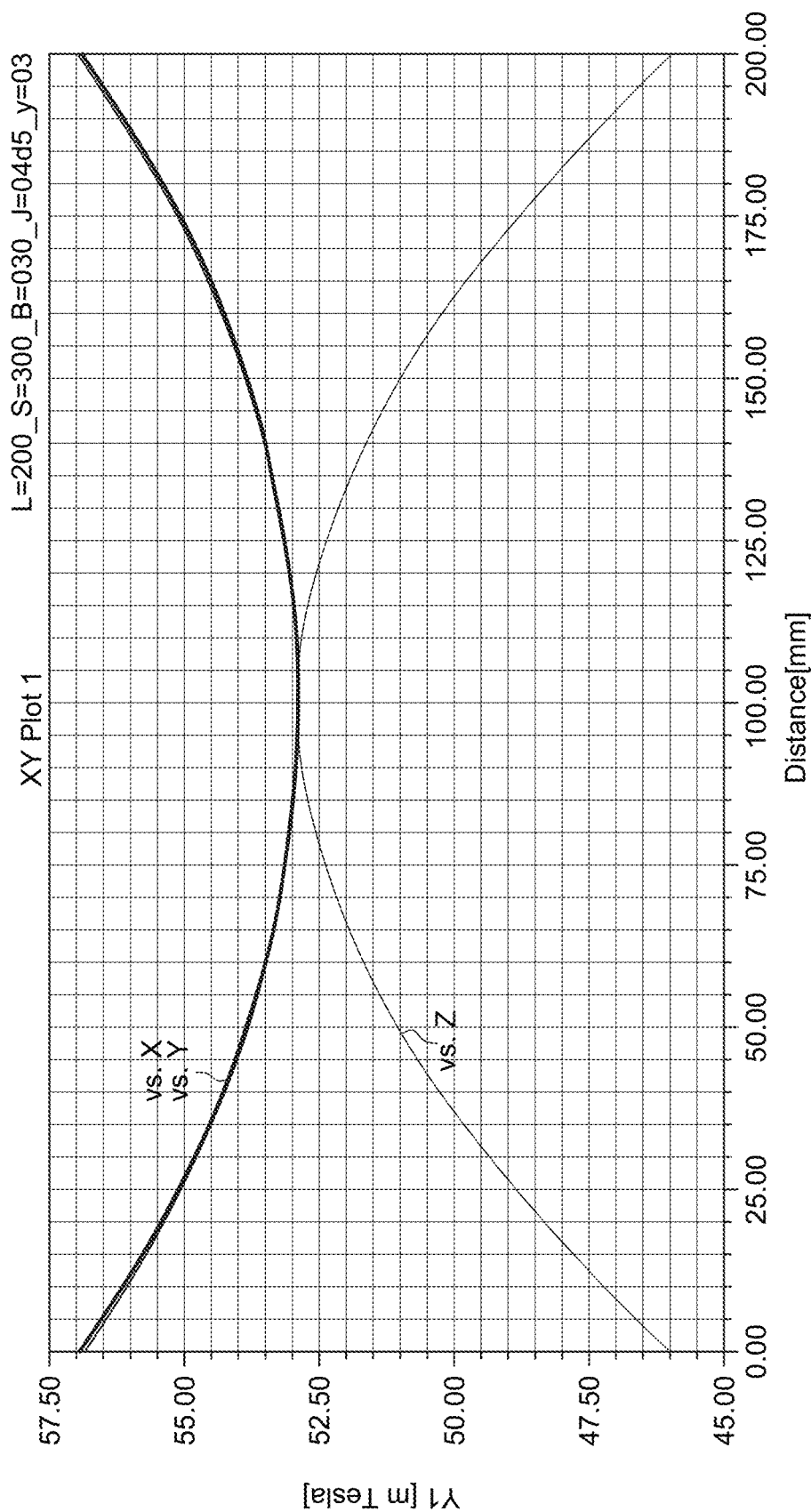

FIG. 19 shows magnitude distribution versus 3 coordinate axis xyz.

The system according to FIG. 9 through FIG. 19 has the following characteristics:

TABLE 1

| | | |
|---|---|---|
| Permanent magnet weight: | $48 * 7{,}500 [kg/m^3] * 2.77 * 10^{-4} [m^3] =$ | 100 kg |
| Yoke weight: | $7{,}800 [kg/m^3] * 1.426 * 10^{-3} [m^3] =$ | 11 kg |
| Coil weight: | $2{,}700 [kg/m^3] * 0.45 * 1.19 * 10^{-2} [m^3] =$ | 14 kg |
| Total active weight: | | 125 kg |
| Drive and cooling fixture weight estimate: | | 25 kg |
| Total system weight: | | 150 kg |
| Power loss: | $2.8 * 10^{-8} [Ohm*m] * (10 * 10^6 \, A/m^2)^2 * 0.45 * 1.19 * 10^{-2} [m^3] =$ | 24 kW |
| Power loss per kg: | | 1.7 kW/kg |

These characteristics again allow for the use of a commercially available water cooling system and the system dimensions and weight allow for installation in regular offices, making it a valid solution in a clinical setting, adhering to the limitations previously discussed.

U-Shaped Coil System

Figure 20:
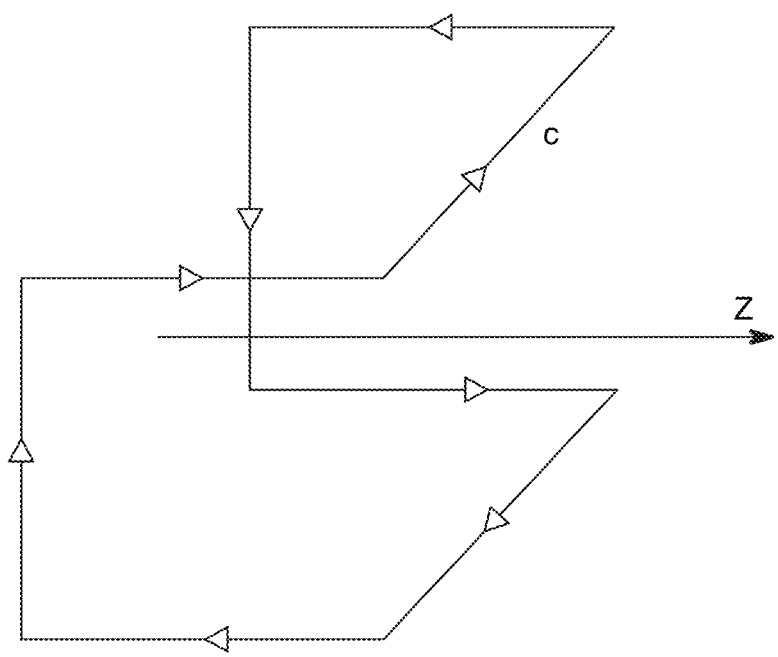
Figure 21:
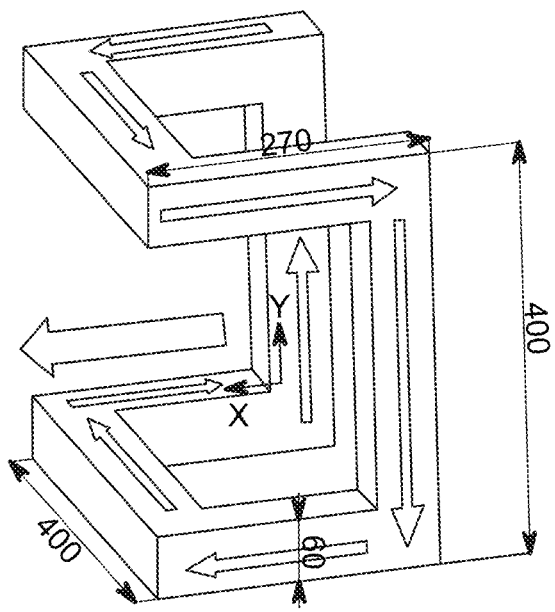
Figure 22:
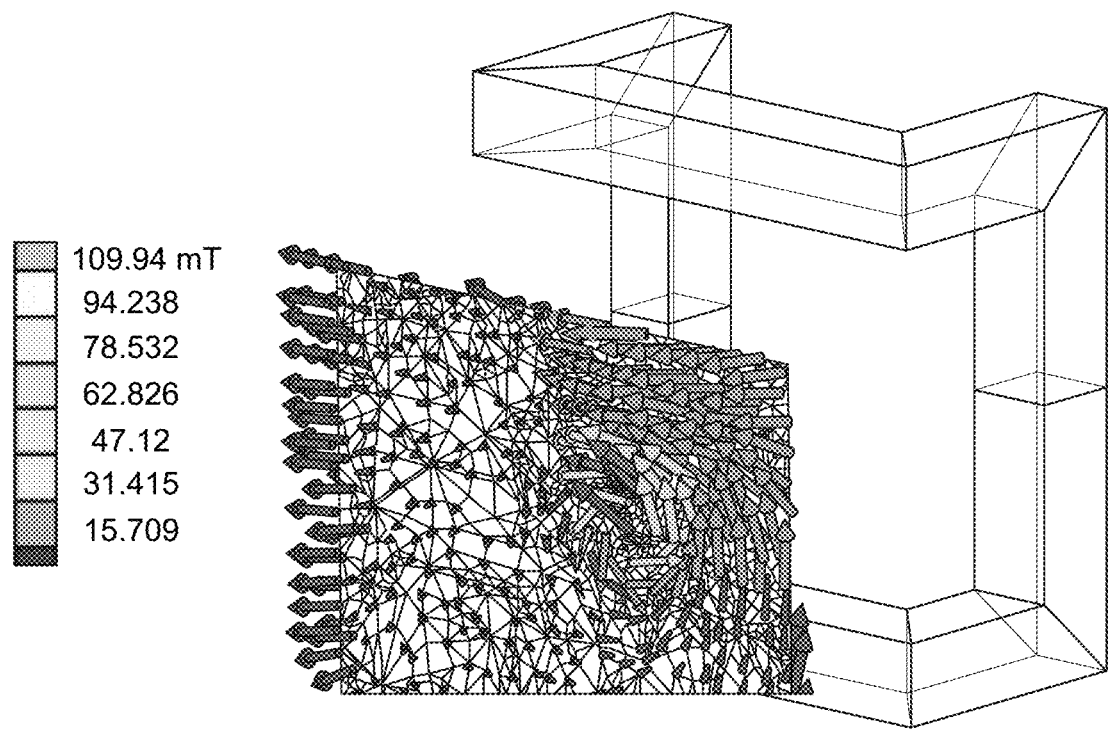

FIG. 20 through FIG. 22 illustrate what is herein denoted as a U-shaped coil system. In order to adhere to the specific weight, size, and power requirements of a human-size clinical system, the standard Helmholtz coils approach (3 pairs of orthogonal coils) must be modified to occupy less space and to generate less heat, while still providing good patient access and still generating sufficiently strong fields in the focus region inside the patient body. According to certain embodiments of the invention, one, two or three of the Helmholtz coil pairs are replaced by a specially-shaped coil (herein denoted as a U-shaped coil), as schematically illustrated in FIG. 20 and described below. A U-shaped coil according to these embodiments of the invention maximizes the magnetic field in the direction of the z-axis in FIG. 20. FIG. 20 shows that a U-shaped coil includes 8 substantially straight segments adjoined end-to-end to form a single closed electrical circuit, wherein:

- a first set of four segments thereof are mutually parallel (in the z-axis), and two subsets thereof each carry two anti-parallel currents;
- a second set of two segments thereof are mutually parallel (in the x-axis), carry two anti-parallel currents, and are orthogonal to the first set; and
- a third set of two segments thereof are mutually parallel (in the y-axis), carry two anti-parallel currents, and are orthogonal to the first set and to the second set.

It is understood that a U-shaped coil can include a multiple-turn winding, in a similar fashion as that of an ordinary coil.

FIG. 21 shows the dimensions of a human-size U-shaped coil in a representative embodiment. FIG. 22 shows the results of a FEA simulation, demonstrating high magnetic field stability along the z-axis (as defined in FIG. 20), in a particular focus plane.

Figure 23:
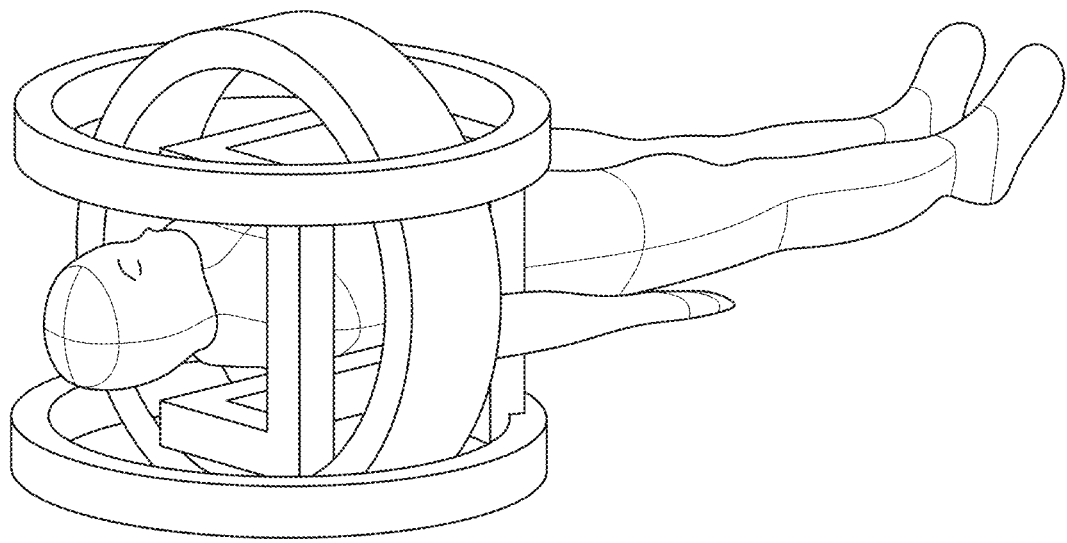

The advantage of such system is the ability to generate a strong magnetic field in an operational region fitting a human patient, while the entire system is more compact, weighs less and generates less heat. FIG. 23 shows an example of such setup, where the U-shaped coil takes much less space than a pair of Helmholtz coils (see FIG. 2A, FIG. 2B, 3 for reference), and fits around the patient body.

As shown in FIG. 23, the different coils and system components may need to be assembled before operation around patient body, by automatically sliding to their position after the patient is positioned on the bed (instead of the patient sliding into a pre-assembled system). In the configuration of FIG. 23, a pair of Helmholtz coils (e.g., FIG. 1A) are replaced by a single U-shape coil. In a related embodiment, a pair of Helmholtz coils is replaced by a single coil around the patient body, allowing a shift the patient body position relative to the system along the patient symmetry axis, and hence a shift in the focus region in the patient body. Thus, this configuration has three types of coil: a U-shaped coil, a single round solenoid coil (around the patient body), and a pair of Helmholtz coils (above and below the patient body).

Figure 24:
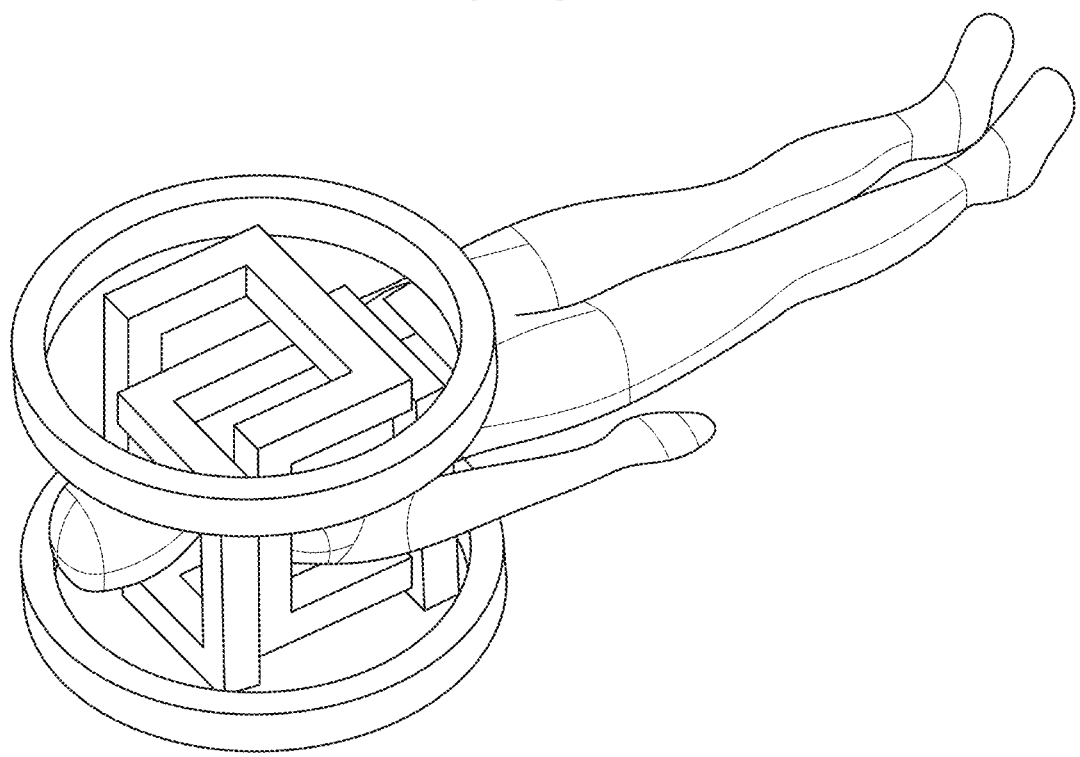

The design can further be utilized for other coils in the system. FIG. 24 shows another embodiment where two of the three Helmholtz coil pairs have been replaced by the U-shaped coils, allowing further reduction in weight, size, and heat generation.

Figure 25:
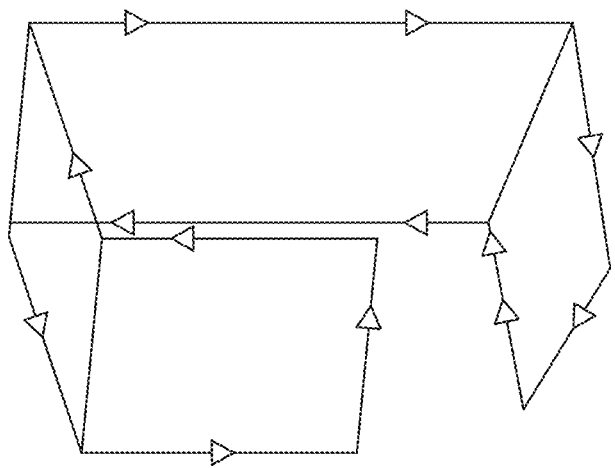
Figure 25:
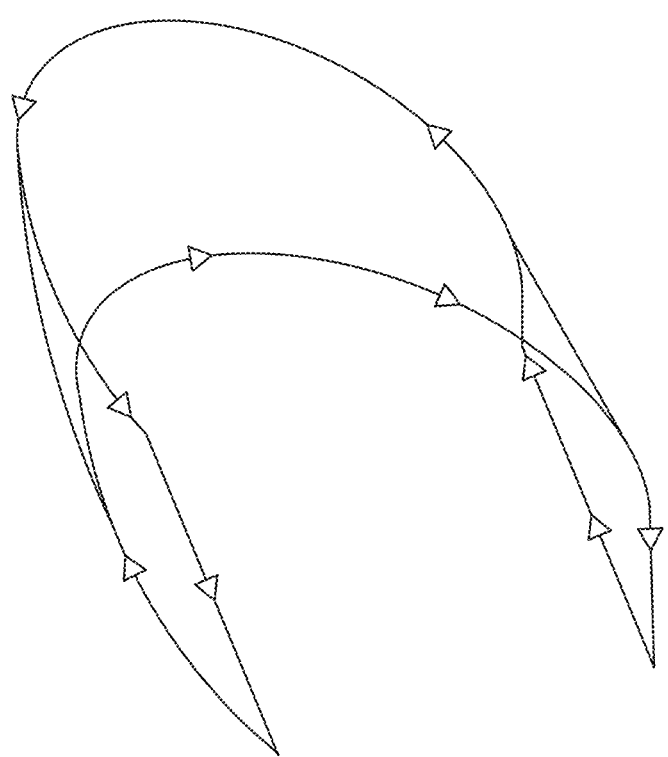

Further embodiments provide changing the coil shape to fit around the patient body, and provide other topologies, including the use of semi-circular shapes, or shapes enclosing the patient body on four sides (instead of three sides, as in the embodiments discussed above). Non-limiting examples of a few such shapes and the direction of current are shown in FIG. 25.

Another embodiment of a coil-based system as illustrated in the drawings provides MRI imaging of the operational region in addition to remote motion control/remote power transfer/uplink and downlink communication or any combination thereof, as described above and illustrated in the drawings.

A related embodiment further utilizes NMR effects for imaging by introducing alternative strong magnetic field gradient to monitor the resulting measurable nuclear Larmor frequencies and to analyze them into a 3D image of different materials. Another related embodiment includes an additional strong permanent magnet and uses the coil systems as previously described to create the required perturbation. In an alternative embodiment, the coil system induces a strong magnetic field and the required perturbation. A further embodiment is used in conjunction with additional markers for reference to allow for alignment of the resulting images. In some embodiments, the coil system fits into an existing MRI device to use its infrastructure of permanent magnets or superconducting coils.

Another embodiment includes a hybrid system comprising an electromagnetic mechanism only for part of the functionality (such as the embodiments described above and illustrated in the drawings), while other functionalities are provided using other mechanisms (such as Ultrasound, Optical, etc.).

In a further embodiment, the coil system is used as an add-on module to augment, improve or allow multiple alternative means of propulsion, imaging, communication and safety. A related embodiment is used with a threaded device, wherein the thread is used for data transfer, power transfer, as means of locating the internal device, as means of extended safety or a combination of these. In other embodiments, the coil system is used to provide the above features while some or all of the power transfer or propulsion inducing is performed via ultrasonic devices such as micro-cavitation induced motion, or mechanical motion using micro propellers.

Other means of communication can be used in parallel, in addition or instead of the abovementioned devices, such as ultrasonic communications, optical communications and specifically utilizing wavelengths with low absorption in water and lipids such as some NIR frequencies, thread communications and others.

What is claimed is:

1. An electromagnetic control system for remote control of a micro-scale device, comprising:
    an imaging system adapted to track a location of the micro-scale device;
    at least one U-shaped coil, wherein the at least one U-shaped coil includes 8 substantially straight segments adjoined end-to-end to form a single closed electrical circuit, wherein:
    a first set of four segments are mutually parallel, and two subsets thereof each carry two anti-parallel currents;
    a second set of two segments thereof are mutually parallel, carry two anti-parallel currents, and are orthogonal to the first set; and
    a third set of two segments thereof are mutually parallel, carry two anti-parallel currents, and are orthogonal to the first set and to the second set; and
    a remote control station and an interface adapted to receive input from the imaging system and transfer energy to the coils to direct movement of the micro-scale device in the magnetic field.

2. The electromagnetic control system according to claim 1, further comprising a Halbach array.

3. The electromagnetic control system according to claim 1, further comprising Helmholtz or Maxwell coils.

4. The electromagnetic control system according to claim 1, further comprising two sets of coils, each of the two sets of coils being in a planar configuration.

5. The electromagnetic control system according to claim 1, comprising a plurality of U-shaped coils.

6. The electromagnetic control system according to claim 1, wherein the U-shaped coil is adapted to at least partially surround a patient body.

7. The electromagnetic control system according to claim 1, further comprising:
    at least one micro-scale device having a dimension between 1 nm and 10 mm;
    wherein the at least one micro-scale device has a magnetic moment and is adapted to be implanted in a patient body.

8. The electromagnetic control system according to claim 7,
    wherein the micro-scale device is selected from a group consisting of:
        a micro- or nano-scale robot,
        a medical tool,
        an implantable device,
        a smart pill; and
        a micropump;
    wherein:
        the micro-scale device is operative to move inside a patient's body;
    and wherein
        the micro-scale device has a magnetic moment substantially in a range from $10^{-7}$ Nm/T to $10^{-4}$ Nm/T.

9. The electromagnetic control system according to claim 7, adapted for remote power transfer to the micro-scale device, further comprising an internal element in the micro-scale device selected from a group consisting of:
    an inductively coupled coil,
    a resonant inductive system, and
    a magneto-dynamic rotational coupling system;
    wherein the internal element is adapted to receive transmitted energy from a magnetic field generating device.

10. The electromagnetic control system according to claim 7, adapted for data communication with the micro-scale device in a patient's body, and further comprising a radio-frequency identification (RFID) integrated circuit (IC) on the micro-scale device, wherein the RFID IC is adapted to transmit information relating to a condition of the micro-scale device.

11. The electromagnetic control system according to claim 7, adapted for uplink and downlink data communication with the micro-scale device in a patient body, and further comprising a micro Hall sensor on an integrated circuit (IC) on the micro-scale device, wherein the IC is adapted to receive information from the magnetic signal, decode the information, and transmit a response to the electromagnetic control system.

12. The electromagnetic control system according to claim 7, wherein the micro-scale device contains a magnetic field sensor comprising three micro-components oriented according to respective orthogonal axes on the micro-scale device.

13. The electromagnetic control system according to claim 12, wherein a micro-component is selected from a group consisting of:
    a Hall sensor,
    a coil,
    an inductively coupled coil,
    a resonant inductive system, and
    a magneto-dynamic rotational coupling system.

14. A method of directing movement of a micro-scale device in a patient body, the method comprising:
    providing an electromagnetic control system with a micro-scale device according to claim 7;
    inserting the micro-scale device into the patient body; and
    applying a magnetic field generated by the electromagnetic control system to the micro-scale device to direct movement of the micro-scale device in the magnetic field.

15. The method of claim 14, further comprising locating the micro-scale device in the patient body with the imaging system of the electromagnetic control system.

* * * * *